US006593119B2

(12) United States Patent
Korczak et al.

(10) Patent No.: US 6,593,119 B2
(45) Date of Patent: Jul. 15, 2003

(54) CORE 2 β-1,6-N-ACETYLGLYCOSAMINYLTRANSFERASE GENE

(75) Inventors: Bozena Korczak, Toronto (CA); April Lew, Toronto (CA)

(73) Assignee: Glycodesign, Inc., Toronto (CA)

( * ) Notice: Subject to any disclaimer, the term of this patent is extended or adjusted under 35 U.S.C. 154(b) by 0 days.

(21) Appl. No.: 09/793,998

(22) Filed: Feb. 28, 2001

(65) Prior Publication Data

US 2002/0045202 A1 Apr. 18, 2002

Related U.S. Application Data

(60) Provisional application No. 60/185,702, filed on Feb. 29, 2000.

(51) Int. Cl.[7] .................. C12N 9/10; C12N 15/79; C12N 5/10; C07H 21/04; C12Q 1/48
(52) U.S. Cl. .................. 435/193; 435/15; 435/320.1; 435/252.3; 435/325; 435/69.1; 536/23.2
(58) Field of Search .................. 536/23.2; 435/19.3, 435/15, 320.1, 252.3, 325, 69.1

(56) References Cited

U.S. PATENT DOCUMENTS

| | | | |
|---|---|---|---|
| 5,360,733 A | 11/1994 | Fukuda et al. | 435/193 |
| 5,624,832 A | 4/1997 | Fukuda et al. | 435/193 |
| 5,658,778 A | 8/1997 | Fukuda et al. | 435/193 |
| 5,684,134 A | 11/1997 | Fukuda et al. | 530/388.26 |
| 6,136,580 A | 10/2000 | Fukuda et al. | 435/193 |

FOREIGN PATENT DOCUMENTS

| | | |
|---|---|---|
| CA | 2145657 | 9/1993 |
| WO | WO 00/34449 | 6/2000 |
| WO | WO 01/14535 | 3/2001 |

OTHER PUBLICATIONS

Smith et al., Nature Biotechnology 15:1222–1223, 1997.*
Brenner, TIG 15:132–1333, 1999.*
Blazquez et al., GenEMBL accession No. X57709, Mol. Microbiol. 5:1511–1518, 1991.*
Fukuda et al., GenEMBL accession No. I41262, May 1997.*
DOE Joint Genome Institute, GenEMBL accession No. AC020867, Feb. 16, 2000.*
Williams and Schachter, 1980J. Biol. Chem 255:11247, 1980.
Yousefi et al, 1991 J. Biol. Chem 266: 1772–1782.
Higgins et al, 1991 J. Biol. Chem 266: 6280–6290.
Zhu and Laine, 1985 J. Biol. Chem 260: 4041–4045.
Merkle and Cummings, 1988 J. Biol. Chem 263: 16143–16149.
Whitehouse et al, 1997 J Cell Biol. 137: 1229–1241.
Kumar et al, 1996; Blood 88: 3872–3879.
Nishio Y. et al, J. Clin Invest Oct. 1995; 96(4): 1759–67.
Shimodaira K, et al, Cancer Res. 57: 5201–5206, 1997.
Koenderman et al., FEBS Lett. 222:42, 1987.
Palcic et al Glycoconjugate 5:49, 1988.
Pierce et al, Biochem. Biophys. Res. Comm. 146: 679, 1987.
Yeh, et al., J. Biological Chemistry, vol. 274, No. 5, 3215–3221 1999.
Schwientek et al, J. Biological Chemistry, vol. 274, No. 5, 4504–4512 1999.
Laferte and Dennis, 1988 Cancer Research 48: 4743–4748.
Li et al, 1996 J. Biol. Chem. 271: 3255–3264.
Schachter H. et al, Glycoconjugates. Composition, Structure, and Function. Marcel Dekker, New York, pp. 263–332 1992.
Bowen, et al, Anticancer Research 17: 4345–4346 (1977).
Goss, et al, Cancer Research 54, 1450–1457, Mar. 15, 1994.

\* cited by examiner

*Primary Examiner*—Rebecca E. Prouty
*Assistant Examiner*—Delia Ramirez
(74) *Attorney, Agent, or Firm*—Millen, White, Zelano & Branigan, P.C.

(57) ABSTRACT

Novel core 2 β-1,6-N-acetylglycosaminyltransferase nucleic acids, polypeptides encoded by the nucleic acids, and uses of the nucleic acids and polypeptides.

14 Claims, 2 Drawing Sheets

CORE 2 β-1,6-N-ACETYLGLYCOSAMINYLTRANSFERASE GENE

This application claims the benefit of the filing date of U.S. Provisional Application Ser. No. 60/185,702 filed Feb. 29, 2000.

FIELD OF THE INVENTION

The invention relates to novel core 2 β-1,6-N-acetylglycosaminyltransferase nucleic acid molecules, polypeptides encoded by such nucleic acid molecules, and uses of the nucleic acid molecules and polypeptides.

BACKGROUND OF THE INVENTION

The enzyme UDP-GlcNAc:Gal[β] 1,3GalNAc-R (GlcNAc to GalNAc) [β] 1,6-N-acetylglucosaminyltransferase (i.e. core 2 β-1,6-N-acetylglycosaminyltransferase) converts core 1 (i.e. Gal[β] 1,3GalNAc[α]-O) to core 2 structures (i.e. Gal[β]1,3 [GlcNAc[β]1,6]GalNAc[α]-O in the O-linked glycan biosynthesis pathway (Williams and Schachter, 1980 J. Biol. Chem 255:11247, 1980 and Schachter H. and Brockhausen, I, In: Allen,, H. J. and Kisailus, E. C. (eds) Glycoconjugates. Composition, Structure, and Function. Marcel Dekker, New York, pp 263–332). Core 2 GlcNAc-T activity is important in the extension of O-linked sugars with poly(N-acetyllactosamine) (i.e. repeating Gal [β] 1-4GlcNAc [β] 1-3). These structures have been associated with malignant transformation (Yousefi et al, 1991) and proliferative activation of lymphocytes (Higgins et al, 1991), they affect cellular adhesion (Zhu and Laine, 1985; Laferte and Dennis, 1988), and they may act as ligands for mammalian lectins (Merkle and Cummings, 1988)

Synthesis of branched, complex core 2-based O-linked structures has been found to be controlled by the relative levels of core 2 GlcNAc-T and [α]-2,3 sialyl-T (Whitehouse et al, 1997) which compete for the same core 1 acceptor substrate. Therefore, core 2 is a key enzyme in the modulation of cell—cell interactions through glycosylation of target molecules. For example, glycosylation of PSGL-1 modulated by core 2 GlcNAc-T has been found to be a critical step for binding to P-selectin (Kumar et al, 1996; Li et al, 1996).

Expression of Core 2 GlcNAc-T in diabetic heart has also been associated with a stress-response and myocardial hypertrophy (Nishio Y. et al, J. Clin Invest 1995 October; 96(4): 1759–67). Diabetes and hyperglycemia induces core 2 GlcNAc-T gene expression specifically in cardiac myocytes of rats.

GalNAcαR prevents core 2 synthesis by blocking one enzyme earlier in the O-linked pathway, and it reduces invasion and metastasis. A somatic mutation that prevents UDP-Gal transport into the Golgi blocking O- and N-linked extensions including core 2 structures causes a more severe attenuation of metastasis than a block in either pathway alone, suggesting both O-linked core 2 and N-linked branched oligosaccharides contribute to the malignant phenotype. Most recently, it was demonstrated that an increased expression of core 2 GlcNAc-T in colorectal cancer cells is closely correlated with the progression of the disease (Shimodaira K., at al 97, Cancer Res.).

The identification of new core 2 GlcNAc-transferases and nucleic acids encoding the enzymes satisfies a need in the art by providing new compositions which are useful in the diagnosis, prevention, and treatment of disorders mediated by the enzymes including cancer and inflammatory disorders.

The citation of any reference herein is not an admission that such reference is available as prior art to the instant invention.

SUMMARY OF THE INVENTION

The present inventors have identified novel core 2 β-1,6-N-acetylglycosaminyltransferase nucleic acid molecules, and polypeptides encoded by such nucleic acid molecules. The nucleic acid molecules are herein designated "core2c GlcNAc-T" or "core2c GlcNAc-T", and the polypeptides are herein designated "Core 2c", "Core 2c GlcNAc-T", or "Core 2c GlcNAc-T Polypeptide". The core 2c GlcNAc-T nucleic acid molecules were found to be primarily expressed in the placenta, kidney, liver, and thymus.

Broadly stated the present invention contemplates an isolated Core 2c GlcNAc-T nucleic acid molecule encoding a polypeptide of the invention, including mRNAs, DNAs, cDNAs, genomic DNAs, PNAs, as well as antisense analogs and biologically, diagnostically, prophylactically, clinically or therapeutically useful variants or fragments thereof, and compositions comprising same.

The invention also contemplates an isolated Core 2c GlcNAc-T polypeptide encoded by a nucleic acid molecule of the invention a truncation, an analog, an allelic or species variation thereof, or a homolog of a polypeptide of the invention or a truncation thereof. (Truncations, analogs, allelic or species variations, and homologs are collectively referred to herein as "Core 2c GlcNAc-T Related Polypeptides"). The polypeptide comprises cytosolic, transmembrane, and catalytic regions.

The nucleic acid molecules of the invention permit identification of untranslated nucleic acid sequences or regulatory sequences that specifically promote expression of genes operatively linked to the promoter regions. Identification and use of such promoter sequences are particularly desirable in instances, such as gene transfer or gene therapy, which may specifically require heterologous gene expression in a limited environment. The invention therefore contemplates a nucleic acid molecule comprising a non-coding sequence such as a 5' and/or 3" sequence.

The nucleic acid molecules which encode for the mature core 2c GlcNAc-T polypeptide (may include only the coding sequence for the mature polypeptide (SEQ ID NO. 1, 7 or 10); the coding sequence for the mature polypeptide and additional coding sequences (e.g. leader or secretory sequences, proprotein sequences); the coding sequence for the mature polypeptide (and optionally additional coding sequence) and non-coding sequence, such as introns or non-coding sequence 5' and/or 3' of the coding sequence of the mature polypeptide (e.g. SEQ ID NO. 9).

Therefore, the term "nucleic acid molecule encoding a polypeptide" encompasses a nucleic acid molecule which includes only coding sequence for the polypeptide as well as a nucleic acid molecule which includes additional coding and/or non-coding sequences.

The nucleic acid molecules of the invention may be inserted into an appropriate vector, and the vector may contain the necessary elements for the transcription and translation of an inserted coding sequence. Accordingly, vectors may be constructed which comprise a nucleic acid molecule of the invention, and where appropriate one or more transcription and translation elements linked to the nucleic acid molecule.

Vectors are contemplated within the scope of the invention which comprise regulatory sequences of the invention, as well as chimeric gene constructs wherein a regulatory sequence of the invention is operably linked to a heterologous nucleic acid, and a transcription termination signal.

A vector can be used to transform host cells to express a Core 2c GlcNAc-T Polypeptide or Core 2c GlcNAc-T Related Polypeptide, or a heterologous polypeptide (i.e. a polypeptide not naturally expressed in the host cell). Therefore, the invention further provides host cells containing a vector of the invention. The invention also contemplates transgenic non-human mammals whose germ cells and somatic cells contain a vector comprising a nucleic acid molecule of the invention in particular one that encodes an analog of Core 2c GlcNAc-T, or a truncation of Core 2c GlcNAc-T.

The polypeptides of the invention may be obtained as an isolate from natural cell sources, but they are preferably produced by recombinant procedures. In one aspect the invention provides a method for preparing a Core 2c GlcNAc-T Polypeptide, or a Core 2c GlcNAc-T Related Polypeptide utilizing the purified and isolated nucleic acid molecules of the invention. In an embodiment a method for preparing a Core 2c GlcNAc-T Polypeptide, or a Core 2c GlcNAc-T Related Polypeptide is provided comprising:

(a) transferring a vector of the invention comprising a nucleic acid sequence encoding a Core 2c GlcNAc-T Polypeptide, or Core 2c GlcNAc-T Related Polypeptide, into a host cell;

(b) selecting transformed host cells from untransformed host cells;

(c) culturing a selected transformed host cell under conditions which allow expression of the Core 2c GlcNAc-T Polypeptide, or Core 2c GlcNAc-T Related Polypeptide; and (d) isolating the Core 2c GlcNAc-T Polypeptide, or a Core 2c GlcNAc-T Related Polypeptide.

The invention further broadly contemplates a recombinant Core 2c GlcNAc-T Polypeptide, or a Core 2c GlcNAc-T Related Polypeptide obtained using a method of the invention.

A Core 2c GlcNAc-T Polypeptide, or a Core 2c GlcNAc-T Related Polypeptide of the invention may be conjugated with other molecules, such as polypeptides, to prepare fusion polypeptides or chimeric polypeptides. This may be accomplished, for example, by the synthesis of N-terminal or C-terminal fusion polypeptides.

The invention further contemplates antibodies having specificity against an epitope of a Core 2c GlcNAc-T Polypeptide, or a Core 2c GlcNAc-T Related Polypeptide of the invention. Antibodies may be labeled with a detectable substance and used to detect polypeptides of the invention in biological samples, tissues, and cells.

The invention also permits the construction of nucleotide probes that are unique to nucleic acid molecules of the invention and/or to polypeptides of the invention. Therefore, the invention also relates to a probe comprising a sequence encoding a polypeptide of the invention, or a portion (i.e. fragment) thereof. The probe may be labeled, for example, with a detectable substance and it may be used to select from a mixture of nucleic acid molecules a nucleic acid molecule of the invention including nucleic acid molecules coding for a polypeptide which displays one or more of the properties of a polypeptide of the invention.

In accordance with an aspect of the invention there is provided a method of, and products for (i.e. kits), diagnosing and monitoring conditions mediated by core 2c GlcNAc-transferases by determining the presence of nucleic acid molecules and polypeptides of the invention.

Still further the invention provides a method for evaluating a test compound for its ability to modulate the biological activity of a Core 2c GlcNAc-T Polypeptide, or a Core 2c GlcNAc-T Related Polypeptide of the invention. For example, a substance which inhibits or enhances the catalytic activity of a Core 2c GlcNAc-T Polypeptide, or a Core 2c GlcNAc-T Related Polypeptide may be evaluated. "Modulate" refers to a change or an alteration in the biological activity of a polypeptide of the invention. Modulation may be an increase or a decrease in activity, a change in characteristics, or any other change in the biological, functional, or immunological properties of the polypeptide.

Compounds which modulate the biological activity of a polypeptide of the invention may also be identified using the methods of the invention by comparing the pattern and level of expression of a nucleic acid molecule or polypeptide of the invention in biological samples, tissues and cells, in the presence, and in the absence of the compounds.

Methods are also contemplated that identify compounds or substances (e.g. polypeptides) which interact with core 2c regulatory sequences (e.g. promoter sequences, enhancer sequences, negative modulator sequences, see SEQ ID NO. 9).

The nucleic acid molecules, polypeptides, and substances and compounds identified using the methods of the invention, may be used to modulate the biological activity of a Core 2c GlcNAc-T Polypeptide, or a Core 2c GlcNAc-T Related Polypeptide of the invention, and they may be used in the treatment of conditions mediated by core 2c GlcNAc-Transferases such as inflammatory disorders, liver disorders, kidney disorders, disorders of the thymus, and proliferative disorders such as cancer. Accordingly, the nucleic acid molecules, polypeptides, substances and compounds may be formulated into compositions for administration to individuals suffering from one or more of these conditions. Therefore, the present invention also relates to a composition comprising one or more of a polypeptide, nucleic acid molecule, or substance or compound identified using the methods of the invention, and a pharmaceutically acceptable carrier, excipient or diluent. A method for treating or preventing these conditions is also provided comprising administering to a patient in need thereof, a composition of the invention.

The present invention in another aspect provides means necessary for production of gene-based therapies directed at the placenta, liver, kidney, and thymus. These therapeutic agents may take the form of polynucleotides comprising all or a portion of a nucleic acid molecule of the invention comprising a regulatory sequence of core 2c GlcNAc-T placed in appropriate vectors or delivered to target cells in more direct ways.

Having provided a novel Core 2c GlcNAc-T Polypeptide, and nucleic acids encoding same, the invention accordingly further provides methods for preparing oligosaccharides e.g. two or more saccharides including sLe$^x$ antigens. In specific embodiments, the invention relates to a method for preparing an oligosaccharide comprising contacting a reaction mixture comprising a sugar donor, and an acceptor in the presence of a Core 2c GlcNAc-T Polypeptide, or a Core 2c GlcNAc-T Related Polypeptide of the invention.

In accordance with a further aspect of the invention, there are provided processes for utilizing polypeptides or nucleic acid molecules, for in vitro purposes related to scientific research, synthesis of DNA, and manufacture of vectors.

These and other aspects, features, and advantages of the present invention should be apparent to those skilled in the art from the following drawings and detailed description.

DESCRIPTION OF THE DRAWINGS

The invention will be better understood with reference to the drawings in which.

DETAILED DESCRIPTION OF THE INVENTION

Figure 1:
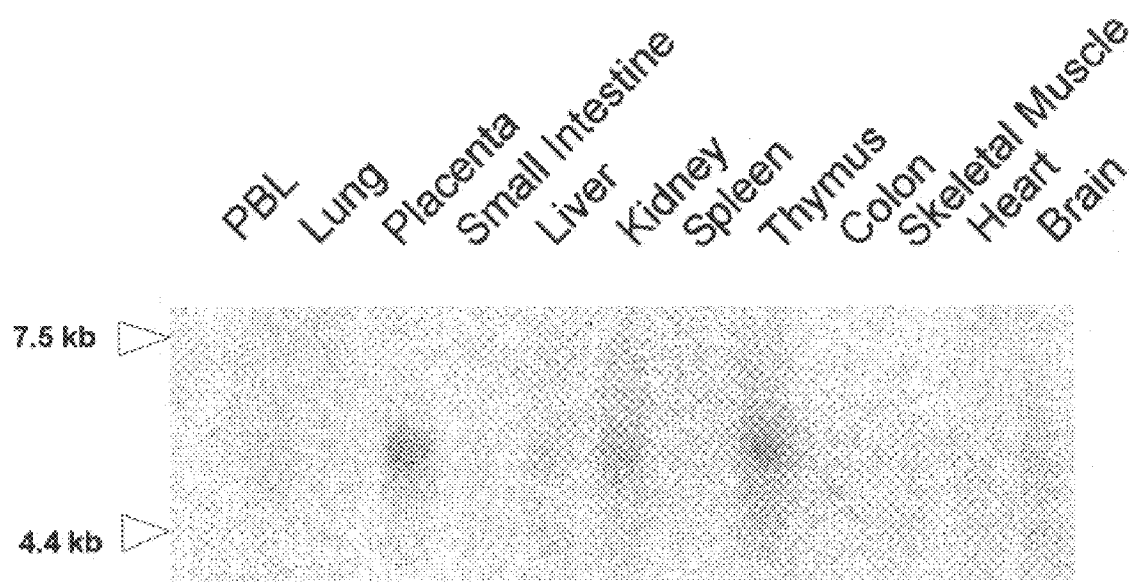
FIG. 1 is a blot showing expression of core2c GlcNAc-T mRNA in human tissues.

In accordance with the present invention there may be employed conventional molecular biology, microbiology, and recombinant DNA techniques within the skill of the art. Such techniques are explained fully in the literature. See for example, Sambrook, Fritsch, & Maniatis, Molecular Cloning: A Laboratory Manual, Second Edition (1989) Cold Spring Harbor Laboratory Press, Cold Spring Harbor, N.Y.); DNA Cloning: A Practical Approach, Volumes I and II (D. N. Glover ed. 1985); Oligonucleotide Synthesis (M. J. Gait ed. 1984); Nucleic Acid Hybridization B. D. Hames & S. J. Higgins eds. (1985); Transcription and Translation B. D. Hames & S. J. Higgins eds (1984); Animal Cell Culture R. I. Freshney, ed. (1986); Immobilized Cells and enzymes IRL Press, (1986); and B. Perbal, A Practical Guide to Molecular Cloning (1984).

Nucleic Acid Molecules of the Invention

As hereinbefore mentioned, the invention provides isolated Core 2c GlcNAc-T nucleic acid molecules. The term "isolated" refers to a nucleic acid (or polypeptide) removed from its natural environment, purified or separated, or substantially free of cellular material or culture medium when produced by recombinant DNA techniques, or chemical reactants, or other chemicals when chemically synthesized. Preferably, an isolated nucleic acid is at least 60% free, more preferably at least 75% free, and most preferably at least 90 to 99% free from other components with which they are naturally associated. The term "nucleic acid" is intended to include modified or unmodified DNA, RNA, including mRNAs, DNAs, cDNAs, and genomic DNAs, or a mixed polymer, and can be either single-stranded, double-stranded or triple-stranded. For example, a nucleic acid sequence may be a single-stranded or double-stranded DNA, DNA that is a mixture of single-and double-stranded regions, or single-, double- and triple-stranded regions, single- and double-stranded RNA, RNA that may be single-stranded, or more typically, double-stranded, or triple-stranded, or a mixture of regions comprising RNA or DNA, or both RNA and DNA. The strands in such regions may be from the same molecule or from different molecules. The DNAs or RNAs may contain one or more modified bases. For example, the DNAs or RNAs may have backbones modified for stability or for other reasons. A nucleic acid sequence includes an oligonucleotide, nucleotide, or polynucleotide. The term "nucleic acid molecule" and in particular DNA or RNA, refers only to the primary and secondary structure and it does not limit it to any particular tertiary forms.

In an embodiment of the invention an isolated nucleic acid molecule is contemplated which comprises:

(i) a nucleic acid sequence encoding a polypeptide having substantial sequence identity with the amino acid sequence of SEQ. ID. NO. 2, 8 or 11;

(ii) a nucleic acid sequence complementary to (i);

(iii) a nucleic acid sequence differing from any of (i) or (ii) in codon sequences due to the degeneracy of the genetic code;

(iv) a nucleic acid sequence comprising at least 10, 15, 18, preferably at least 20 nucleotides capable of hybridizing to a nucleic acid sequence of SEQ. ID. NO. 1, 7, or 10 or to a degenerate form thereof;

(v) a nucleic acid sequence encoding a truncation, an analog, an allelic or species variation of a polypeptide comprising the amino acid sequence of SEQ. ID. NO. 2, 8, or 11; or (vi) a fragment, or allelic or species variation of (i), (ii) or (iii)

In a specific embodiment, the isolated nucleic acid molecule comprises:

(i) a nucleic acid sequence having substantial sequence identity or sequence similarity with a nucleic acid sequence of SEQ. ID. NO. 1, 7, or 10;

(ii) nucleic acid sequences complementary to (i), preferably complementary to the full nucleic acid sequence of SEQ. ID. NO. 1, 7, or 10;

(iii) nucleic acid sequences differing from any of the nucleic acid sequences of (i) or (ii) in codon sequences due to the degeneracy of the genetic code; or (iv) a fragment, or allelic or species variation of (i), (ii) or (iii).

In a preferred embodiment a nucleic acid molecule is provided comprising or consisting essentially of the nucleic acid sequence of SEQ ID NO. 1, 7, or 10.

The term "complementary" refers to the natural binding of nucleic acid molecules under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules.

In a preferred embodiment the isolated nucleic acid comprises a nucleic acid sequence encoded by the amino acid sequence of SEQ. ID. NO. 2, 8, or 11, or comprises the nucleic acid sequence of SEQ. ID. NO. 1, 7, or 10 wherein T can also be U.

The terms "sequence similarity" or "sequence identity" refer to the relationship between two or more amino acid or nucleic acid sequences, determined by comparing the sequences, which relationship is generally known as "homology". Identity in the art also means the degree of sequence relatedness between amino acid or nucleic acid sequences, as the case may be, as determined by the match between strings of such sequences. Both identity and similarity can be readily calculated (Computational Molecular Biology, Lesk, A.M., ed., Oxford University Press New York, 1988; Biocomputing: Informatics and Genome Projects, Smith, D. W. ed., Academic Press, New York, 1993; Computer Analysis of Sequence Data, Part I, Griffin, A.M., and Griffin, H. G. eds. Humana Press, New Jersey, 1994; Sequence Analysis in Molecular Biology, von Heinje, G., Academic Press, New York, 1987; and Sequence Analysis Primer, Gribskov, M. and Devereux, J., eds. M. Stockton Press, New York, 1991). While there are a number of existing methods to measure identity and similarity between two amino acid sequences or two nucleic acid sequences, both terms are well known to the skilled artisan (Sequence Analysis in Molecular Biology, von Heinje, G., Academic Press, New York, 1987; Sequence Analysis Primer, Gribskov, M. and Devereux, J., eds. M. Stockton Press, New York, 1991; and Carillo, H., and Lipman, D. SIAM J. Applied Math., 48:1073, 1988). Preferred methods for determining identity are designed to give the largest match between the sequences tested. Methods to determine identity are codified in computer programs. Preferred computer program methods for determining identity and similarity between two sequences include but are not limited to the GCG program package (Devereux, J. et al, Nucleic Acids Research 12(1): 387, 1984), BLASTP, BLASTN, and FASTA (Atschul, S. F. et al., J. Molec. Biol. 215:403, 1990). Identity or similarity may also be determined using the alignment algorithm of Dayhoff et al [Methods in Enzymology 91: 524–545 (1983)].

Preferably, the nucleic acids of the present invention have substantial sequence identity using the preferred computer programs cited herein, for example greater than 22%, 25%, 30%, 35%, 40%, 45%, 50%, 60%, 70%, 75%, 80%, 85%, or 90% identity; more preferably at least 95%, 96%, 97%, 98%, or 99% sequence identity to the sequence of SEQ. ID. NO. 1, 7, or 10.

Isolated nucleic acids encoding a Core 2c GlcNAc-T Polypeptide and comprising a sequence that differs from the nucleic acid sequence of SEQ. ID. NO. 1, 7, or 10 due to degeneracy in the genetic code are also within the scope of the invention. Such nucleic acids encode equivalent polypeptides but differ in sequence from the sequence of SEQ. ID. NO. 1, 7, or 10 due to degeneracy in the genetic code. As one example, DNA sequence polymorphisms within core2c GlcNAc-T may result in silent mutations that do not affect the amino acid sequence. Variations in one or more nucleotides may exist among individuals within a population due to natural allelic variation. Any and all such nucleic acid variations are within the scope of the invention. DNA sequence polymorphisms may also occur which lead to changes in the amino acid sequence of Core 2c GlcNAc-T Polypeptide. These amino acid polymorphisms are also within the scope of the present invention. In addition, species variations i.e. variations in nucleotide sequence naturally occurring among different species, are within the scope of the invention.

Another aspect of the invention provides a nucleic acid molecule which hybridizes under selective conditions, (e.g. high stringency conditions), to a nucleic acid which comprises a sequence which encodes a Core 2c GlcNAc-T Polypeptide of the invention. Preferably the sequence encodes the amino acid sequence of SEQ. ID. NO. 2, 8, or 11 and comprises at least 10, 15, 18, and preferably at least 20 nucleotides. Selectivity of hybridization occurs with a certain degree of specificity rather than being random. Appropriate stringency conditions which promote DNA hybridization are known to those skilled in the art, or can be found in Current Protocols in Molecular Biology, John Wiley & Sons, N.Y. (1989), 6.3.1–6.3.6. For example, hybridization may occur at 30° C. in 750 mM NaCl, 75 mM trisodium citrate, and 1% SDS, preferably 37° C. in 500 mM NaCl, 500 mM trisodium citrate, 1% SDS, 35% formamide, and 100 µg/ml denatured salmon sperm DNA (ssDNA), and more preferably 42° C. in 250 mM NaCl, 25 mM trisodium citrate, 1% SDS, 50% formamide, and 200 µg/ml ssDNA. Useful variations on these conditions will be readily apparent to those skilled in the art.

The stringency may be selected based on the conditions used in the wash step. Wash step stringency conditions may be defined by salt concentration and by temperature. Generally, wash stringency can be increased by decreasing salt concentration or by increasing termperature. By way of example, a stringent salt concentration for the wash step is preferably less than about 30 mM NaCl and 3 mM trisodium citrate, and more preferably less than about 15 mM NaCl and 1.5 mM trisodium citrate. Stringent temperature conditions will generally include temperatures of a least about 25° C., more preferably at least about 68° C. In a preferred embodiment, the wash steps will be carried out at 42° C. in 15 mM NaCl, 1.5 mM trisodium citrate, and 0.1% SDS. In a more preferred embodiment the wash steps are carried out at 68° C. in 15 mM NaCl, 1.5 mM trisodium citrate, and 0.1% SDS. Variations on these conditions will be readily apparent to those skilled in the art.

It will be appreciated that the invention includes nucleic acid molecules encoding a Core 2c GlcNAc-T Polypeptide, or a Core 2c GlcNAc-T Related Polypeptide, including truncations of the polypeptides, allelic and species variants, and analogs of the polypeptides as described herein. In particular, fragments of a nucleic acid of the invention are contemplated that are a stretch of at least about 10, 15, or 18, and preferably at least 20 nucleotides, more typically at least 50 to 200 nucleotides but less than 2 kb. It will further be appreciated that variant forms of the nucleic acid molecules of the invention which arise by alternative splicing of an mRNA corresponding to a cDNA of the invention are encompassed by the invention.

An isolated nucleic acid molecule of the invention which comprises DNA can be isolated by preparing a labeled nucleic acid probe based on all or part of the nucleic acid sequence of SEQ. ID. NO. 1, 7, or 10. The labeled nucleic acid probe is used to screen an appropriate DNA library (e.g. a cDNA or genomic DNA library). For example, a cDNA library can be used to isolate a cDNA encoding a Core 2c GlcNAc-T Polypeptide, or a Core 2c GlcNAc-T Related Polypeptide by screening the library with the labeled probe using standard techniques. Alternatively, a genomic DNA library can be similarly screened to isolate a genomic clone encompassing a core2 gene. Nucleic acids isolated by screening of a cDNA or genomic DNA library can be sequenced by standard techniques.

An isolated nucleic acid molecule of the invention that is DNA can also be isolated by selectively amplifying a nucleic acid of the invention. "Amplifying" or "amplification" refers to the production of additional copies of a nucleic acid sequence and is generally carried out using polymerase chain reaction (PCR) technologies well known in the art (Dieffenbach, C. W. and G. S. Dveksler (1995) PCR Primer, a Laboratory Manual, Cold Spring Harbor Press, Plainview, N.Y.). In particular, it is possible to design synthetic oligonucleotide primers from the nucleotide sequence shown in SEQ. ID. NO. 1, 7, or 10 for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. cDNA may be prepared from mRNA, by isolating total cellular mRNA by a variety of techniques, for example, by using the guanidinium-thiocyanate extraction procedure of Chirgwin et al., Biochemistry, 18, 5294–5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated nucleic acid molecule of the invention which is RNA can be isolated by cloning a cDNA encoding a Core 2c GlcNAc-T Polypeptide, or a Core 2c GlcNAc-T Related Polypeptide into an appropriate vector which allows for transcription of the cDNA to produce an RNA molecule which encodes a Core 2c GlcNAc-T Polypeptide, or a Core 2c GlcNAc-T Related Polypeptide. For example, a cDNA can be cloned downstream of a bacteriophage promoter, (e.g. a T7 promoter) in a vector, cDNA can be transcribed in vitro with T7 polymerase, and the resultant RNA can be isolated by conventional techniques.

A nucleic acid molecule of the invention may be engineered using methods known in the art to alter the core-2c encoding sequence for a variety of purposes including modification of the cloning, processing, and/or expression of the gene product. Procedures such as DNA shuffling by random fragmentation and PCR reassembly of gene fragments and synthetic oligonucleotides may be used to engineer the nucleic acid molecules. Mutations may be introduced by oligonucleotide-mediated site-directed mutagenesis to create for example new restriction sites, alter glycosylation patterns, change codon preference, or produce splice variants.

Nucleic acid molecules of the invention may be chemically synthesized using standard techniques. Methods of chemically synthesizing polydeoxynucleotides are known, including but not limited to solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

Determination of whether a particular nucleic acid molecule is a core2c or encodes a Core 2c GlcNAc-T Polypeptide, or a Core 2c GlcNAc-T Related Polypeptide can be accomplished by expressing the cDNA in an appropriate host cell by standard techniques, and testing the expressed polypeptide in the methods described herein. A core 2c GlcNAc-T cDNA, or cDNA encoding a Core 2c GlcNAc-T Polypeptide, or a Core 2c GlcNAc-T Related Polypeptide, can be sequenced by standard techniques, such as dideoxynucleotide chain termination or Maxam-Gilbert chemical sequencing, to determine the nucleic acid sequence and the predicted amino acid sequence of the encoded polypeptide.

The nucleic acid molecules of the invention may be extended using a partial nucleotide sequence and various PCR-based methods known in the art to detect upstream sequences such as promoters and regulatory elements. For example, restriction-site PCR which uses universal and nested primers to amplify unknown sequences from genomic DNA within a cloning vector may be employed (See Sarkar, G, PCR Methods Applic. 2:318–322, 1993). Inverse PCR which uses primers that extend in divergent directions to amplify unknown sequences from a circularized template may also be used. The template in inverse PCR is derived from restriction fragments adjacent to known sequences in human and yeast artificial chromosome DNA (See e.g. Lagerstrom, M., at al, PCR Methods Applic. 1:111–119, 1991). Other methods for retrieving unknown sequences are known in the art (e.g. Parker, J. D. et al, Nucleic Acids Res. 19:305–306, 1991). In addition, PCR, nested primers, and PROMOTERFINDER libraries (Clontech, Palo Alto, Calif.) may be used to walk genomic DNA. The method is useful in finding intron/exon junctions and avoids the need to screen libraries.

It is preferable when screening for full-length cDNAs to use libraries that have been size-selected to include larger cDNAs. For situations in which an oligo d(T) library does not yield a full-length cDNA, it is preferable to use random-primed libraries which often include sequences containing the 5' regions of genes. Genomic libraries may be useful for extending the sequence into 5'non-translated regulatory regions.

Commercially available capillary electrophoresis systems may be employed to analyse the size or confirm the sequence of PCR or sequencing products. The system may use flowable polymers for electrophoretic separation, four different nucleotide-specific, laser-stimulated fluorescent dyes, and a charge coupled device camera for detection of the emitted wavelengths. Commercially available software (e.g. GENOTYPER and SEQUENCE NAVIGATOR, Perkin-Elmer) may convert the output/light intensity to electrical signal, and the entire process from loading of samples, and computer analysis and electronic data display may be computer controlled. This procedure may be particularly useful for sequencing small DNA fragments which may be present in limited amounts in a particular sample.

In accordance with one aspect of the invention, a nucleic acid molecule is provided comprising a core 2c GlcNAc-T regulatory sequence such as a promoter sequence.

In an embodiment, a nucleic acid molecule is provided which comprises (i) a nucleic acid sequence having substantial sequence identity or sequence similarity with a nucleic acid sequence of SEQ ID NO. 9; (ii) nucleic acid sequences complementary to (i), preferably complementary to the full nucleic acid sequence of SEQ ID NO. 9; (iii) nucleic acid sequences differing from any of the nucleic acid sequences of (i) and (ii) in codon sequences due to the degeneracy of the genetic code; or (iv) a fragment, or allelic or species variation of (i), (ii), or (iii). In a preferred embodiment a nucleic acid molecule is provided comprising or consisting essentially of the nucleic acid sequence of SEQ ID NO. 9.

The invention contemplates nucleic acid molecules comprising all or a portion of a nucleic acid molecule of the invention comprising a regulatory sequence of a core 2c GlcNAc-T contained in appropriate vectors. The vectors may contain heterologous nucleic acid sequences. "Heterologous nucleic acid" refers to a nucleic acid not naturally located in the cell, or in a chromosomal site of the cell. Preferably, the heterologous nucleic acid includes a nucleic acid foreign to the cell.

In accordance with another aspect of the invention, the nucleic acid molecules isolated using the methods described herein are mutant core2c gene alleles. For example, the mutant alleles may be isolated from individuals either known or proposed to have a genotype which contributes to the symptoms of a condition such as an inflammatory disorder, liver disorder, kidney disorder, disorder of the placenta, disorder of the thymus, or cancer. Mutant alleles and mutant allele products may be used in therapeutic and diagnostic methods described herein. For example, a cDNA of a mutant core 2c GlcNAc-T gene may be isolated using PCR as described herein, and the DNA sequence of the mutant allele may be compared to the normal allele to ascertain the mutation(s) responsible for the loss or alteration of function of the mutant gene product. A genomic library can also be constructed using DNA from an individual suspected of or known to carry a mutant allele, or a cDNA library can be constructed using RNA from tissue known, or suspected to express the mutant allele. A nucleic acid encoding a normal core 2c GlcNAc-T gene or any suitable fragment thereof, may then be labeled and used as a probe to identify the corresponding mutant allele in such libraries. Clones containing mutant sequences can be purified and subjected to sequence analysis. In addition, an expression library can be constructed using cDNA from RNA isolated from a tissue of an individual known or suspected to express a mutant core2 allele. Gene products from putatively mutant tissue may be expressed and screened, for example using antibodies specific for a Core 2c GlcNAc-T Polypeptide, or a Core 2c GlcNAc-T Related Polypeptide as described herein. Library clones identified using the antibodies can be purified and subjected to sequence analysis.

Antisense molecules and ribozymes are contemplated within the scope of the invention. They may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding core2c GlcNAc-T. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues. RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Polypeptides of the Invention

The polypeptides of the invention are predominately expressed in the placenta, kidney, liver, and thymus.

The amino acid sequence of an isolated Core 2c GlcNAc-T Polypeptide of the invention comprises the sequence of SEQ.ID. NO. 2, 8, or 11. In addition to polypeptides comprising the amino acid sequence of SEQ.ID. NO. 2, 8, or 11, the polypeptides of the present invention include truncations, and analogs, allelic and species variations, and homologs of Core 2c GlcNAc-T and truncations thereof as described herein (i.e Core 2c GlcNAc-T Related Polypeptide).

Truncated polypeptides may comprise peptides or fragments having an amino acid sequence of at least five consecutive amino acids of SEQ.ID. NO. 2, 8, or 11 where no amino acid sequence of five or more, six or more, seven or more, or eight or more, consecutive amino acids present in the fragment is present in a polypeptide other than Core 2c GlcNAc-T. In an embodiment of the invention the fragment is a stretch of amino acid residues of at least 12 to 50 contiguous amino acids, preferably 12 to 20 contiguous amino acids, from particular sequences such as the sequences of SEQ.ID. NO. 2, 8, or 11. The fragments may be immunogenic and preferably are not immunoreactive with antibodies that are immunoreactive to polypeptides other than Core 2c GlcNAc-T. In an embodiment the fragments correspond to the cytosolic, transmembrane, or catalytic regions of a Core 2c GlcNAc-T Polypeptide.

The truncated polypeptides may have an amino group (—NH2), a hydrophobic group (for example, carbobenzoxyl, dansyl, or T-butyloxycarbonyl), an acetyl group, a 9-fluorenylmethoxy-carbonyl (PMOC) group, or a macromolecule including but not limited to lipid-fatty acid conjugates, polyethylene glycol, or carbohydrates at the amino terminal end. The truncated polypeptides may have a carboxyl group, an amido group, a T-butyloxycarbonyl group, or a macromolecule including but not limited to lipid-fatty acid conjugates, polyethylene glycol, or carbohydrates at the carboxy terminal end.

The polypeptides of the invention may also include analogs of Core 2c GlcNAc-T Polypeptide, and/or truncations thereof as described herein, which may include, but are not limited to Core 2c GlcNAc-T Polypeptide, containing one or more amino acid substitutions, insertions, and/or deletions. Amino acid substitutions may be of a conserved or non-conserved nature. Conserved amino acid substitutions involve replacing one or more amino acids of the Core 2c GlcNAc-T amino acid sequence with amino acids of similar charge, size, and/or hydrophobicity characteristics. When only conserved substitutions are made the resulting analog is preferably functionally equivalent to Core 2c GlcNAc-T. Non-conserved substitutions involve replacing one or more amino acids of the Core 2c GlcNAc-T amino acid sequence with one or more amino acids that possess dissimilar charge, size, and/or hydrophobicity characteristics.

One or more amino acid insertions may be introduced into a Core 2c GlcNAc-T Polypeptide. Amino acid insertions may consist of single amino acid residues or sequential amino acids ranging from about 2 to 15 amino acids in length.

Deletions may consist of the removal of one or more amino acids, or discrete portions from the amino acid sequence. The deleted amino acids may or may not be contiguous. The lower limit length of the resulting analog with a deletion mutation is about amino acids, preferably 100 amino acids.

An allelic variant of Core 2c GlcNAc-T at the polypeptide level differs from one another by only one, or at most, a few amino acid substitutions. A species variation of a Core 2c GlcNAc-T Polypeptide is a variation which is naturally occurring among different species of an organism.

The polypeptides of the invention also include homologs of Core 2c Polypeptide and/or truncations thereof as described herein. Such Core 2c GlcNAc-T homologs include polypeptides whose amino acid sequences are comprised of the amino acid sequences of Core 2c Polypeptide regions from other species that hybridize under selective hybridization conditions (see discussion of selective and in particular stringent hybridization conditions herein) with a probe used to obtain a Core 2c GlcNAc-T Polypeptide. These homologs will generally have the same regions which are characteristic of a Core 2c GlcNAc-T Polypeptide. It is anticipated that a polypeptide comprising an amino acid sequence which has at least 60% identity or at least 70% similarity, preferably at least 60–65% identity or at least 80–85% similarity, more preferably at least 70–80% identity or at least 90–95% similarity, most preferably at least 95% to 99% identity or at least 99% similarity with the amino acid sequence of SEQ. ID. NO. 2, 8, or 11 will be a homolog of a Core 2 Polypeptide. A percent amino acid sequence similarity or identity is calculated using the methods described herein, preferably the computer programs described herein.

The invention also contemplates isoforms of the polypeptides of the invention. An isoform contains the same number and kinds of amino acids as the polypeptide of the invention, but the isoform has a different molecular structure. The isoforms contemplated by the present invention preferably have the same properties as the polypeptide of the invention as described herein.

The present invention also includes Core 2c GlcNAc-T Polypeptide, or a Core 2c GlcNAc-T Related Polypeptide conjugated with a selected polypeptide, or a marker polypeptide (see below), or other glycosyltransferases to produce fusion polypeptides or chimeric polypeptides.

A Core 2c GlcNAc-T Polypeptide, or a Core 2c GlcNAc-T Related Polypeptide of the invention may be prepared using recombinant DNA methods. Accordingly, the nucleic acids of the present invention having a sequence which encodes a Core 2c GlcNAc-T Polypeptide, or a Core 2 Related Polypeptide of the invention may be incorporated in a known manner into an appropriate vector which ensures good expression of the polypeptide. Possible expression vectors include but are not limited to cosmids, plasmids, phages, or modified viruses (e.g. replication defective retroviruses, adenoviruses and adeno-associated viruses), so long as the vector is compatible with the host cell used.

The invention therefore contemplates a vector of the invention containing a nucleic acid molecule of the invention, and the necessary regulatory sequences for the transcription and translation of the inserted polypeptide-sequence. Suitable regulatory sequences may be derived from a variety of sources, including bacterial, fungal, viral, mammalian, or insect genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen as discussed below, and may be readily accomplished by one of ordinary skill in the art. The necessary regulatory sequences may be supplied by the native Core 2c GlcNAc-T Polypeptide and/or its flanking regions (e.g. SEQ ID NO 9).

The invention further provides a vector comprising a nucleic acid of the invention cloned into the expression vector in an antisense orientation. That is, the DNA molecule is linked to a regulatory sequence in a manner which allows for expression, by transcription of the DNA molecule, of an RNA molecule which is antisense to the nucleic acid sequence of SEQ. ID. NO. 1, 7, or 10. Regulatory sequences linked to the antisense nucleic acid can be chosen which direct the continuous expression of the antisense RNA molecule in a variety of cell types, for instance a viral promoter and/or enhancer, or regulatory sequences can be chosen which direct tissue or cell type specific expression of antisense RNA.

The vectors of the invention may also contain a marker gene which facilitates the selection of host cells transformed or transfected with a recombinant molecule of the invention. Examples of marker genes are genes encoding a polypeptide such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. The markers can be introduced on a separate vector from the nucleic acid of interest.

The vectors may also contain genes that encode a fusion moiety which provides increased expression of the recombinant polypeptide; increased solubility of the recombinant polypeptide; and aid in the purification of the target recombinant polypeptide by acting as a ligand in affinity purification. For example, a proteolytic cleavage site may be added to the target recombinant polypeptide to allow separation of the recombinant polypeptide from the fusion moiety subsequent to purification of the fusion polypeptide. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant polypeptide.

The vectors may be introduced into host cells to produce a transformed or transfected host cell. The terms "transfected" and "transfection" encompass the introduction of nucleic acid (e.g. a vector) into a cell by one of many standard techniques. A cell is "transformed" by a nucleic acid when the transfected nucleic acid effects a phenotypic change. Prokaryotic cells can be transfected or transformed with nucleic acid by, for example, electroporation or calcium-chloride mediated transformation. Nucleic acid can be introduced into mammalian cells via conventional techniques such as calcium phosphate or calcium chloride coprecipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Human artificial chromosomes (HACs) may also be employed to deliver larger fragments of DNA that can be contained and expressed in a plasmid. HACs of 6 to 10M are constructed and delivered via conventional delivery methods (liposomes, polycationic amino polymers, or vesicles) for therapeutic purposes.

Suitable host cells include a wide variety of prokaryotic and eukaryotic host cells. For example, the polypeptides of the invention may be expressed in bacterial cells such as *E. coli*, insect cells (using baculovirus), yeast cells or mammalian cells. Other suitable host cells can be found in Goeddel, Gene Expression Technology: Methods in Enzymology 185, Academic Press, San Diego, Calif. (1991).

A host cell may also be chosen which modulates the expression of an inserted nucleic acid sequence, or modifies (e.g. glycosylation or phosphorylation) and processes (e.g. cleaves) the polypeptide in a desired fashion. Host systems or cell lines may be selected which have specific and characteristic mechanisms for post-translational processing and modification of polypeptides. For example, eukaryotic host cells including CHO, VERO, HL60, BHK, A431, HeLA, COS, MDCK, 293, 3T3, and WI38 may be used. For long-term high-yield stable expression of the polypeptide, cell lines and host systems which stably express the gene product may be engineered.

Host cells and in particular cell lines produced using the methods described herein may be particularly useful in screening and evaluating substances and compounds that modulate the activity of a Core 2c GlcNAc-T Polypeptide, or a Core 2c GlcNAc-T Related Polypeptide.

The polypeptides of the invention may also be expressed in non-human transgenic animals including but not limited to mice, rats, rabbits, guinea pigs, micro-pigs, goats, sheep, pigs, non-human primates (e.g. baboons, monkeys, and chimpanzees) (see Hammer et al. (Nature 315:680–683, 1985), Palmiter et al. (Science 222:809–814, 1983), Brinster et al. (Proc Natl. Acad. Sci USA 82:44384442, 1985), Palmiter and Brinster (Cell. 41:343–345, 1985) and U.S. Pat. No. 4,736,866). Procedures known in the art may be used to introduce a nucleic acid molecule of the invention encoding a Core 2c GlcNAc-T Polypeptide, or a Core 2c GlcNAc-T Related Polypeptide into animals to produce the founder lines of transgenic animals. Such procedures include pronuclear microinjection, retrovirus mediated gene transfer into germ lines, gene targeting in embryonic stem cells, electroporation of embryos, and sperm-mediated gene transfer.

The present invention contemplates a transgenic animal that carries the core 2c GlcNAc-T gene in all their cells, and animals which carry the transgene in some but not all their cells. The transgene may be integrated as a single transgene or in concatamers. The transgene may be selectively introduced into and activated in specific cell types (See for example, Lasko et al, 1992 Proc. Natl. Acad. Sci. USA 89:

6236). The transgene may be integrated into the chromosomal site of the endogenous gene by gene targeting. The transgene may be selectively introduced into a particular cell type inactivating the endogenous gene in that cell type (See Gu et al Science 265: 103–106).

The expression of a recombinant Core 2c GlcNAc-T Polypeptide, or a Core 2c GlcNAc-T Related Polypeptide in a transgenic animal may be assayed using standard techniques. Initial screening may be conducted by Southern Blot analysis, or PCR methods to analyze whether the transgene has been integrated. The level of mRNA expression in the tissues of transgenic animals may also be assessed using techniques including Northern blot analysis of tissue samples, in situ hybridization, and RT-PCR. Tissues may also be evaluated immunocytochemically using antibodies against a Core 2c GlcNAc-T Polypeptide, or a Core 2c GlcNAc-T Related Polypeptide of the invention.

Polypeptides of the invention may also be prepared by chemical synthesis using techniques well known in the chemistry of polypeptides such as solid phase synthesis (Merrifield, 1964, J. Am. Chem. Assoc. 85:2149–2154) or synthesis in homogenous solution (Houbenweyl, 1987, Methods of Organic Chemistry, ed. E. Wansch, Vol. 15 I and II, Thieme, Stuttgart).

N-terminal or C-terminal fusion polypeptides or chimeric polypeptides comprising a Core 2c GlcNAc-T Polypeptide, or a Core 2c GlcNAc-T Related Polypeptide of the invention conjugated with other molecules, such as polypeptides (e.g. markers or other glycosyltransferases) may be prepared by fusing, through recombinant techniques, the N-terminal or C-terminal of a Core 2c GlcNAc-T Polypeptide, or a Core 2c GlcNAc-T Related Polypeptide, and the sequence of a selected polypeptide or marker polypeptide with a desired biological function. The resultant fusion polypeptides contain a Core 2c GlcNAc-T Polypeptide, or a Core 2c GlcNAc-T Related Polypeptide fused to the selected polypeptide or marker polypeptide as described herein. Examples of polypeptides which may be used to prepare fusion polypeptides include immunoglobulins, glutathione-S-transferase (GST), protein A, hemagglutinin (HA), and truncated myc.

Antibodies

A polypeptide of the invention (including fragments) can be used to prepare antibodies specific for the polypeptides. Antibodies can be prepared which bind a distinct epitope in an unconserved region of the polypeptide. An unconserved region of the polypeptide is one that does not have substantial sequence homology to other polypeptides. A region from a conserved region such as a well-characterized sequence can also be used to prepare an antibody to a conserved region of a polypeptide of the invention.

In an embodiment of the invention, oligopeptides, peptides, or fragments used to induce antibodies to a polypeptide of the invention have an amino acid sequence consisting of at least 5 amino acids and more preferably at least 10 amino acids. The oligopeptides, etc. can be identical to a portion of the amino acid sequence of the natural protein, and they may contain the entire amino acid sequence of a small, naturally occurring molecule. Antibodies having a specificity for a polypeptide of the invention may also be raised from fusion polypeptides created by expressing fusion polypeptides in host cells as described herein.

The invention can employ intact monoclonal or polyclonal antibodies, and immunologically active fragments (e.g. a Fab or (Fab)$_2$ fragment), an antibody heavy chain, and antibody light chain, a genetically engineered single chain F$_v$ molecule (Ladner et al, U.S. Pat. No. 4,946,778), or a chimeric antibody, for example, an antibody which contains the binding specificity of a murine antibody, but in which the remaining portions are of human origin. Antibodies, including monoclonal and polyclonal antibodies, fragments and chimeras, may be prepared using methods known to those skilled in the art.

Applications of the Nucleic Acid Molecules, Polypeptides, and Antibodies of the Invention The nucleic acid molecules, Core 2c GlcNAc-T Polypeptide, or a Core 2c GlcNAc-T Related Polypeptide, and antibodies of the invention may be used in the prognostic and diagnostic evaluation of conditions associated with altered expression or activity of a polypeptide of the invention or conditions requiring modulation of a nucleic acid or polypeptide of the invention including inflammatory and proliferative disorders, liver and kidney disorders, disorders of the placenta, and disorders of the thymus, and the identification of subjects with a predisposition to such conditions (See below). Methods for detecting nucleic acid molecules and polypeptides of the invention, can be used to monitor such conditions by detecting and localizing the polypeptides and nucleic acids. It would also be apparent to one skilled in the art that the methods described herein may be used to study the developmental expression of the polypeptides of the invention and, accordingly, will provide further insight into the role of the polypeptides. The applications of the present invention also include methods for the identification of substances or compounds that modulate the biological activity of a polypeptide of the invention (See below). The substances, compounds, antibodies etc., may be used for the treatment of conditions requiring modulation of polypeptides of the invention. (See below).

Diagnostic Methods

A variety of methods can be employed for the diagnostic and prognostic evaluation of conditions requiring modulation of a nucleic acid or polypeptide of the invention (e.g. inflammatory disorders, liver disorders, kidney disorders, disorders of the placenta, disorders of the thymus, and cancer), and the identification of subjects with a predisposition to such conditions. Such methods may, for example, utilize nucleic acid molecules of the invention, and fragments thereof, and antibodies directed against polypeptides of the invention, including peptide fragments. In particular, the nucleic acids and antibodies may be used, for example, for: (1) the detection of the presence of core 2c GlcNAc-T mutations, or the detection of either over- or under-expression of core 2c GlcNAc-T mRNA relative to a non-disorder state or the qualitative or quantitative detection of alternatively spliced forms of core 2c GlcNAc-T transcripts which may correlate with certain conditions or susceptibility toward such conditions; or (2) the detection of either an over- or an under-abundance of a polypeptide of the invention relative to a non-disorder state or the presence of a modified (e.g., less than full length) polypeptide of the invention which correlates with a disorder state, or a progression toward a disorder state.

The methods described herein may be performed by utilizing pre-packaged diagnostic kits comprising at least one specific nucleic acid or antibody described herein, which may be conveniently used, e.g., in clinical settings, to screen and diagnose patients and to screen and identify those individuals exhibiting a predisposition to developing a disorder.

Nucleic acid-based detection techniques and peptide detection techniques are described below. The samples that may be analyzed using the methods of the invention include those that are known or suspected to express core 2c GlcNAc-T or contain a polypeptide of the invention. The methods may be performed on biological samples including but not limited to cells, lysates of cells which have been incubated in cell culture, chromosomes isolated from a cell (e.g. a spread of metaphase chromosomes), genomic DNA (in solutions or bound to a solid support such as for Southern analysis), RNA (in solution or bound to a solid support such as for northern analysis), cDNA (in solution or bound to a solid support), an extract from cells or a tissue, and biological fluids such as serum, urine, blood, and CSF. The samples may be derived from a patient or a culture.

Methods for Detecting Nucleic Acid Molecules of the Invention

A nucleic acid molecule encoding a polypeptide of the invention may be used in Southern or northern analysis, dot blot, or other membrane-based technologies; in PCR technologies; or in dipstick, pin, ELISA assays or microarrays utilizing fluids or tissues from patient biopsies to detect altered expression. Such qualitative or quantitative methods are well known in the art and some methods are described below.

The nucleic acid molecules of the invention allow those skilled in the art to construct nucleotide probes for use in the detection of nucleic acid sequences of the invention in biological materials. Suitable probes include nucleic acid molecules based on nucleic acid sequences encoding at least 5 sequential amino acids from regions of the Core 2c GlcNAc-T Polypeptide, or a Core 2c GlcNAc-T Related Polypeptide (see SEQ. ID. No. 1, 3, 4, 5, 6, 7, or 10), preferably they comprise 15 to 50 nucleotides, more preferably 15 to 40 nucleotides, most preferably 15–30 nucleotides. A nucleotide probe may be labeled with a detectable substance such as a radioactive label that provides for an adequate signal and has sufficient half-life such as $^{32}P$, $^{3}H$, $^{14}C$ or the like. Other detectable substances that may be used include antigens that are recognized by a specific labeled antibody, fluorescent compounds, enzymes, antibodies specific for a labeled antigen, and luminescent compounds. An appropriate label may be selected having regard to the rate of hybridization and binding of the probe to the nucleotide to be detected and the amount of nucleotide available for hybridization. Labeled probes may be hybridized to nucleic acids on solid supports such as nitrocellulose filters or nylon membranes as generally described in Sambrook et al, 1989, Molecular Cloning, A Laboratory Manual (2nd ed.). The nucleic acid probes may be used to detect core 2c GlcNAc-T genes, preferably in human cells. The nucleotide probes may also be useful for example in the diagnosis or prognosis of conditions such as inflammatory disorders, liver disorders, kidney disorders, disorders of the placenta, disorders of the thymus, and cancer, and in monitoring the progression of these conditions, or monitoring a therapeutic treatment.

The probe may be used in hybridization techniques to detect a core 2c GlcNAc-T gene. The technique generally involves contacting and incubating nucleic acids (e.g. recombinant DNA molecules, cloned genes) obtained from a sample from a patient or other cellular source with a probe of the present invention under conditions favourable for the specific annealing of the probes to complementary sequences in the nucleic acids. After incubation, the non-annealed nucleic acids are removed, and the presence of nucleic acids that have hybridized to the probe if any are detected.

The detection of nucleic acid molecules of the invention may involve the amplification of specific gene sequences using an amplification method (e.g. PCR), followed by the analysis of the amplified molecules using techniques known to those skilled in the art. Suitable primers can be routinely designed by one of skill in the art. For example, primers may be designed using commercially available software, such as OLIGO 4.06 Primer Analysis software (National Biosciences, Plymouth Minn.) or another appropriate program, to be about 22 to 30 nucleotides in length, to have a GC content of about 50% or more, and to anneal to the template at temperatures of about 60° C. to 72° C.

Genomic DNA may be used in hybridization or amplification assays of biological samples to detect abnormalities involving core 2c GlcNAc-T structure, including point mutations, insertions, deletions, and chromosomal rearrangements. For example, direct sequencing, single stranded conformational polymorphism analyses, heteroduplex analysis, denaturing gradient gel electrophoresis, chemical mismatch cleavage, and oligonucleotide hybridization may be utilized.

Genotyping techniques known to one skilled in the art can be used to type polymorphisms that are in close proximity to the mutations in a core 2c GlcNAc-T gene. The polymorphisms may be used to identify individuals in families that are likely to carry mutations. If a polymorphism exhibits linkage disequalibrium with mutations in the core 2c GlcNAc-T gene, it can also be used to screen for individuals in the general population likely to carry mutations. Polymorphisms which may be used include restriction fragment length polymorphisms (RFLPs), single-nucleotide polymorphisms (SNP), and simple sequence repeat polymorphisms (SSLPs).

A probe or primer of the invention may be used to directly identify RFLPs. A probe or primer of the invention can additionally be used to isolate genomic clones such as YACs, BACs, PACs, cosmids, phage or plasmids. The DNA in the clones can be screened for SSLPs using hybridization or sequencing procedures.

Hybridization and amplification techniques described herein may be used to assay qualitative and quantitative aspects of core 2c GlcNAc-T expression. For example, RNA may be isolated from a cell type or tissue known to express core 2c GlcNAc-T and tested utilizing the hybridization (e.g. standard Northern analyses) or PCR techniques referred to herein. The techniques may be used to detect differences in transcript size that may be due to normal or abnormal alternative splicing. The techniques may be used to detect quantitative differences between levels of full length and/or alternatively splice transcripts detected in normal individuals relative to those individuals exhibiting symptoms of a disease.

The primers and probes may be used in the above described methods in situ i.e directly on tissue sections (fixed and/or frozen) of patient tissue obtained from biopsies or resections.

Oligonucleotides or longer fragments derived from any of the nucleic acid molecules of the invention may be used as targets in a microarray. The microarray can be used to simultaneously monitor the expression levels of large numbers of genes and to identify genetic variants, mutations, and polymorphisms. The information from the microarray may be used to determine gene function, to understand the genetic basis of a disorder, to diagnose a disorder, and to develop and monitor the activities of therapeutic agents.

The preparation, use, and analysis of microarrays are well known to a person skilled in the art. (See, for example, Brennan, T. M. et al. (1995) U.S. Pat. No. 5,474,796; Schena, et al. (1996) Proc. Natl. Acad. Sci. 93:10614–10619; Baldeschweiler et al. (1995), PCT Application WO95/251116; Shalon, D. et al. (I 995) PCT application WO95/35505; Heller, R. A. et al. (1997) Proc. Natl. Acad. Sci. 94:2150–2155; and Heller, M. J. et al. (1997) U.S. Pat. No. 5,605,662.)

Methods for Detecting Polypeptides

Antibodies specifically reactive with a Core 2c GlcNAc-T Polypeptide, a Core 2c GlcNAc-T Related Polypeptide, or derivatives, such as enzyme conjugates or labeled derivatives, may be used to detect Core 2c GlcNAc-T Polypeptides or Core 2c GlcNAc-T Related Polypeptides in various biological materials. They may be used as diagnostic or prognostic reagents and they may be used to detect abnormalities in the level of Core 2c GlcNAc-T Polypeptides or Core 2c GlcNAc-T Related Polypeptides, expression, or abnormalities in the structure, and/or temporal, tissue, cellular, or subcellular location of the polypeptides. Antibodies may also be used to screen potentially therapeutic compounds in vitro to determine their effects on a condition such as an inflammatory disorder, liver disorder, kidney disorder, disorder of the placenta, disorder of the thymus, or cancer. In vitro immunoassays may also be used to assess or monitor the efficacy of particular therapies. The antibodies of the invention may also be used in vitro to determine the level of Core 2c GlcNAc-T Polypeptide or Core 2c GlcNAc-T Related Polypeptide expression in cells genetically engineered to produce a Core 2c GlcNAc-T Polypeptide or Core 2c GlcNAc-T Related Polypeptide.

The antibodies may be used in any known immunoassays that rely on the binding interaction between an antigenic determinant of a polypeptide of the invention, and the antibodies. Examples of such assays are radioimmunoassays, enzyme immunoassays (e.g. ELISA), immunofluorescence, immunoprecipitation, latex agglutination, hemagglutination, and histochemical tests. The antibodies may be used to detect and quantify polypeptides of the invention in a sample in order to determine their role in particular cellular events or pathological states, and to diagnose and treat such pathological states.

In particular, the antibodies of the invention may be used in immuno-histochemical analyses, for example, at the cellular and sub-subcellular level, to detect a polypeptide of the invention, to localise it to particular cells and tissues, and to specific subcellular locations, and to quantitate the level of expression.

Cytochemical techniques known in the art for localizing antigens using light and electron microscopy may be used to detect a polypeptide of the invention. Generally, an antibody of the invention may be labeled with a detectable substance and a polypeptide may be localised in tissues and cells based upon the presence of the detectable substance. Various methods of labeling polypeptides are known in the art and may be used. Examples of detectable substances include, but are not limited to, the following: radioisotopes (e.g., $^3$H, $^{14}$C, $^{35}$S, $^{125}$I, $^{131}$I), fluorescent labels (e.g., FITC, rhodamine, lanthanide phosphors), luminescent labels such as luminol; enzymatic labels (e.g., horseradish peroxidase, $\beta$-galactosidase, luciferase, alkaline phosphatase, acetylcholinesterase), biotinyl groups (which can be detected by marked avidin e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags). In some embodiments, labels are attached via spacer arms of various lengths to reduce potential steric hindrance. Antibodies may also be coupled to electron dense substances, such as ferritin or colloidal gold, which are readily visualised by electron microscopy.

The antibody or sample may be immobilized on a carrier or solid support which is capable of immobilizing cells, antibodies, etc. For example, the carrier or support may be nitrocellulose, or glass, polyacrylamides, gabbros, and magnetite. The support material may have any possible configuration including spherical (e.g. bead), cylindrical (e.g. inside surface of a test tube or well, or the external surface of a rod), or flat (e.g. sheet, test strip). Indirect methods may also be employed in which the primary antigen-antibody reaction is amplified by the introduction of a second antibody, having specificity for the antibody reactive against a polypeptide of the invention. By way of example, if the antibody having specificity against a polypeptide of the invention is a rabbit IgG antibody, the second antibody may be goat anti-rabbit gamma-globulin labeled with a detectable substance as described herein.

Where a radioactive label is used as a detectable substance, a polypeptide of the invention may be localized by radioautography. The results of radioautography may be quantitated by determining the density of particles in the radioautographs by various optical methods, or by counting the grains.

A polypeptide of the invention may also be detected by assaying for Core 2c GlcNAc-T activity as described herein. For example, a sample may be reacted with an acceptor substrate and a sugar donor under conditions where a Core 2 d GlcNAc-T Polypeptide or Core 2c GlcNAc-T Related Polypeptide is capable of transferring the sugar donor to the acceptor substrate to produce a sugar donor-acceptor substrate complex.

Methods for Identifying or Evaluating Substances/Compounds

The methods described herein are designed to identify substances and compounds that modulate the expression or biological activity of a Core 2c GlcNAc-T Polypeptide or Core 2c GlcNAc-T Related Polypeptide including substances that interfere with, or enhance the expression or activity of a Core 2c GlcNAc-T Polypeptide or Core 2c GlcNAc-T Related Polypeptide.

Substances and compounds identified using the methods of the invention include but are not limited to peptides such as soluble peptides including Ig-tailed fusion peptides, members of random peptide libraries and combinatorial chemistry-derived molecular libraries made of D- and/or L-configuration amino acids, phosphopeptides (including members of random or partially degenerate, directed phosphopeptide libraries), antibodies [e.g. polyclonal, monoclonal, humanized, anti-idiotypic, chimeric, single chain antibodies, fragments, (e.g. Fab, F(ab)$_2$, and Fab expression library fragments, and epitope-binding fragments thereof)], polypeptides, nucleic acids, carbohydrates, and small organic or inorganic molecules. A substance or compound may be an endogenous physiological compound or it may be a natural or synthetic compound.

Substances which modulate a Core 2c GlcNAc-T Polypeptide or Core 2c GlcNAc-T Related Polypeptide can be identified based on their ability to associate with a Core 2c GlcNAc-T Polypeptide or Core 2c GlcNAc-T Related Polypeptide. Therefore, the invention also provides methods for identifying substances that associate with a Core 2c GlcNAc-T Polypeptide or Core 2c GlcNAc-T Related Polypeptide. Substances identified using the methods of the invention may be isolated, cloned and sequenced using conventional techniques. A substance that associates with a polypeptide of the invention may be an agonist or antagonist of the biological or immunological activity of a polypeptide of the invention.

The term "agonist" refers to a molecule that increases the amount of, or prolongs the duration of, the activity of the polypeptide. The term "antagonist" refers to a molecule which decreases the biological or immunological activity of the polypeptide. Agonists and antagonists may include proteins, nucleic acids, carbohydrates, or any other molecules that associate with a polypeptide of the invention.

Substances which can associate with a Core 2c GlcNAc-T Polypeptide or Core 2c GlcNAc-T Related Polypeptide may be identified by reacting a Core 2c GlcNAc-T Polypeptide or Core 2c GlcNAc-T Related Polypeptide with a test substance which potentially associates with a Core 2c GlcNAc-T Polypeptide or Core 2c GlcNAc-T Related Polypeptide, under conditions which permit the association, and removing and/or detecting the associated Core 2c GlcNAc-T Polypeptide or Core 2c GlcNAc-T Related Polypeptide and substance. Substance-polypeptide complexes, free substance, or non-complexed polypeptides may be assayed. Conditions which permit the formation of substance-polypeptide complexes may be selected having regard to factors such as the nature and amounts of the substance and the polypeptide.

The substance-polypeptide complex, free substance or non-complexed polypeptides may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against a polypeptide of the invention or the substance, or labeled polypeptide, or a labeled substance may be utilized. The antibodies, polypeptides, or substances may be labeled with a detectable substance as described above.

A Core 2c GlcNAc-T Polypeptide or Core 2c GlcNAc-T Related Polypeptide, or the substance used in the method of the invention may be insolubilized. For example, a polypeptide, or substance may be bound to a suitable carrier such as agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc. The insolubilized polypeptide or substance may be prepared by reacting the material with a suitable insoluble carrier using known chemical or physical methods, for example, cyanogen bromide coupling.

The invention also contemplates a method for evaluating a compound for its ability to modulate the biological activity of a polypeptide of the invention, by assaying for an agonist or antagonist (i.e. enhancer or inhibitor) of the association of the polypeptide with a substance which associates with the polypeptide. The basic method for evaluating if a compound is an agonist or antagonist of the association of a polypeptide of the invention and a substance that associates with the polypeptide, is to prepare a reaction mixture containing the polypeptide and the substance under conditions which permit the formation of substance-polypeptide complexes, in the presence of a test compound. The test compound may be initially added to the mixture, or may be added subsequent to the addition of the polypeptide and substance. Control reaction mixtures without the test compound or with a placebo are also prepared. The formation of complexes is detected and the formation of complexes in the control reaction but not in the reaction mixture indicates that the test compound interferes with the interaction of the polypeptide and substance. The reactions may be carried out in the liquid phase or the polypeptide, substance, or test compound may be immobilized as described herein.

It will be understood that the agonists and antagonists i.e. inhibitors and enhancers, that can be assayed using the methods of the invention may act on one or more of the interaction sites on the polypeptide or substance including agonist binding sites, competitive antagonist binding sites, non-competitive antagonist binding sites or allosteric sites.

The invention also makes it possible to screen for antagonists that inhibit the effects of an agonist of the interaction of a polypeptide of the invention with a substance which is capable of associating with the polypeptide. Thus, the invention may be used to assay for a compound that competes for the same interacting site of a polypeptide of the invention.

Substances that modulate a Core 2c GlcNAc-T Polypeptide or Core 2c GlcNAc-T Related Polypeptide of the invention can be identified based on their ability to interfere with or enhance the activity of a Core 2c GlcNAc-T Polypeptide or Core 2c GlcNAc-T Related Polypeptide. Therefore, the invention provides a method for evaluating a compound for its ability to modulate the activity of a Core 2c GlcNAc-T Polypeptide or Core 2c GlcNAc-T Related Polypeptide comprising (a) reacting an acceptor and a sugar donor for a Core 2c GlcNAc-T Polypeptide or Core 2c GlcNAc-T Related Polypeptide in the presence of a test substance; (b) measuring the amount of sugar donor transferred to acceptor, and (c) carrying out steps (a) and (b) in the absence of the test substance to determine if the substance interferes with or enhances transfer of the sugar donor to the acceptor by the Core 2c GlcNAc-T Polypeptide or Core 2c GlcNAc-T Related Polypeptide.

Suitable acceptors for use in the methods of the invention are a saccharide, oligosaccharides, polysaccharides, glycopeptides, glycopolypeptides, or glycolipids which are either synthetic with linkers at the reducing end or naturally occurring structures, for example, asialo-agalacto-fetuin glycopeptide. Acceptors will generally comprise β-D-galactosyl-1,3-N-acetyl-D-galactosaminyl-.

The sugar donor may be a nucleotide sugar, dolichol-phosphate-sugar or dolichol-pyrophosphate-oligosaccharide, for example, uridine diphospho-N-acetylglucosamine (UDP-GlcNAc), or derivatives or analogs thereof. The Core 2c GlcNAc-T Polypeptide or Core 2c GlcNAc-T Related Polypeptide may be obtained from natural sources or produced used recombinant methods as described herein.

The acceptor or sugar donor may be labeled with a detectable substance as described herein, and the interaction of the polypeptide of the invention with the acceptor and sugar donor will give rise to a detectable change. The detectable change may be calorimetric, photometric, radiometric, potentiometric, etc. The activity of a Core 2c GlcNAc-T Polypeptide or Core 2c GlcNAc-T Related Polypeptide of the invention may also be determined using methods based on HPLC (Koenderman et al., FEBS Lett. 222:42, 1987) or methods employed synthetic oligosaccharide acceptors attached to hydrophobic aglycones (Palcic et al Glycoconjugate 5:49, 1988; and Pierce et al, Biochem. Biophys. Res. Comm. 146: 679, 1987).

The Core 2c GlcNAc-T Polypeptide or Core 2c GlcNAc-T Related Polypeptide is reacted with the acceptor and sugar donor at a pH and temperature and in the presence of a metal cofactor, usually a divalent cation like manganese, effective for the polypeptide to transfer the sugar donor to the acceptor, and where one of the components is labeled, to produce a detectable change. It is preferred to use a buffer with the acceptor and sugar donor to maintain the pH within the pH range effective for the polypeptides. The buffer, acceptor, and sugar donor may be used as an assay composition. Other compounds such as EDTA and detergents may be added to the assay composition.

The reagents suitable for applying the methods of the invention to evaluate compounds that modulate a Core 2c GlcNAc-T Polypeptide or Core 2c GlcNAc-T Related Polypeptide may be packaged into convenient kits providing the necessary materials packaged into suitable containers. The kits may also include suitable supports useful in performing the methods of the invention.

Substances that modulate a Core 2c GlcNAc-T Polypeptide or Core 2c GlcNAc-T Related Polypeptide can also be identified by treating immortalized cells which express the polypeptide with a test substance, and comparing the morphology of the cells with the morphology of the cells in the absence of the substance and/or with immortalized cells which do not express the polypeptide. Examples of immortalized cells that can be used include lung epithelial cell lines such as Mv1Lu transfected with a vector containing a nucleic acid of the invention. In the absence of an inhibitor the cells show signs of morphologic transformation (e.g. fibroblastic morphology, spindle shape and pile up; the cells are less adhesive to substratum; there is less cell to cell contact in monolayer culture; there is reduced growth-factor requirements for survival and proliferation; the cells grow in soft-agar of other semi-solid medium; there is a lack of contact inhibition and increased apoptosis in low-serum high density cultures; there is enhanced cell motility, and there is invasion into extracellular matrix and secretion of proteases). Substances that inhibit one or more phenotypes may be considered an inhibitor.

A substance that inhibits a Core 2c GlcNAc-T Polypeptide or Core 2c GlcNAc-T Related Polypeptide may be identified by treating a cell which expresses the polypeptide with a test substance, and assaying for complex core 2-based O-linked structures (e.g. repeating Gal[β] 1-4GlcNAc[β]) associated with the cell. The complex core 2-based O-linked structures can be assayed using a substance that binds to the structures (e.g. antibodies). Cells that have not been treated with the substance or which do not express the polypeptide may be employed as controls.

Substances which inhibit transcription or translation of a core 2c gene may be identified by transfecting a cell with an expression vector comprising a recombinant molecule of the invention, including a reporter gene, in the presence of a test substance and comparing the level of expression of the Core 2c GlcNAc-T Polypeptide or Core 2c GlcNAc-T Related Polypeptide, or the expression of the protein encoded by the reporter gene with a control cell transfected with the nucleic acid molecule in the absence of the substance. The method can be used to identify transcription and translation inhibitors of a core 2c gene.

Compositions and Treatments

The substances or compounds identified by the methods described herein, polypeptides, nucleic acid molecules, and antibodies of the invention may be used for modulating the biological activity of a Core2c GlcNAc-T polypeptide or a Core2c GlcNAc-T Related Polypeptide, and they may be used in the treatment of conditions mediated by Core 2c GlcNAc-Transferases. In particular, they may be used to modulate cellular adhesion associated with a number of disorders including inflammatory disorders and cancer.

The term "inflammatory" refers to reactions of both the specific and non-specific defense systems. A specific defense system reaction is a specific immune system reaction to an antigen. Examples of these reactions include antibody response to antigens such as viruses, and delayed-type hypersensitivity. A non-specific defense system reaction is an inflammatory response mediated by leukocytes (including macrophages, eosinophils, and neutrophils) generally incapable of immunological memory. Examples of non-specific reactions include the immediate swelling after a bee sting, and the collection of peripheral mononuclear leukocytes at sites of bacterial infection (pulmonary infiltrates in bacterial pneumonia and pus formation in abscesses).

Treatable disorders include rheumatoid arthritis, post-ischemic leukocyte-mediated tissue damage (reperfusion injury), frost-bite injury or shock, acute leukocyte-mediated lung injury (e.g. adult respiratory distress syndrome (ARDS)), asthma, traumatic shock, septic shock, nephritis, and acute and chronic inflammation including atopic dermatitis, psoriasis, neurotoxicity related to aberrant inflammation, and inflammatory bowel disease. Various platelet-mediated pathologies such as atherosclerosis and clotting can also be treated. The substances and compounds may be useful in minimizing tissue damage accompanying thrombotic disorders. For example, the substances, compounds, antibodies etc. can be of therapeutic value in individuals who have recently experienced stroke, myocardial infarctions, deep vein thrombosis, pulmonary embolism, etc. or in pre-thrombolytic therapy. Inhibitors of Core 2c GlcNAc-T may be useful in reducing angiogenesis as well as leukocyte adhesion and entry into inflamed tissue.

A substance, compound, etc. may be used to treat the secondary effects (e.g. pathological tissue destruction, and/or widespread microcirculatory thrombi and diffuse inflammation) of septic shock or disseminated intravascular coagulation (DIC). Substances compounds, etc. herein may inhibit leukocyte emigration and mitigate tissue damage.

A substance, compound, etc. may also be useful in treating traumatic shock and associated acute tissue injury. Inhibitory substances, compounds etc. may be administered locally or systemically to control tissue damage associated with injuries.

The substances or compounds identified by the methods described herein, antibodies, and polypeptides, and nucleic acid molecules of the invention may be useful in the prevention and treatment of tumors. Tumor metastasis may be inhibited or prevented by inhibiting the adhesion of circulating cancer cells. The substances, compounds, etc. of the invention may be especially useful in the treatment of various forms of neoplasia such as leukemias, lymphomas, melanomas, adenomas, neuroblastoma, glioblastoma, astrocytomas, sarcomas, and carcinomas of solid tissues in patients. In particular the composition may be used for treating malignant melanoma, pancreatic cancer, cervico-uterine cancer, cancer of the liver, kidney, thymus, stomach, lung, rectum, breast, bowel, gastric, thyroid, neck, cervix, salivary gland, bile duct, pelvis, mediastinum, urethra, bronchogenic, bladder, esophagus and colon, and Kaposi's Sarcoma which is a form of cancer associated with HIV-infected patients with Acquired Immune Deficiency Syndrome (AIDS). The substances, compounds, etc. are particularly useful in the prevention and treatment of tumors of the kidney and thymus The substances or compounds identified by the methods described herein, antibodies, and polypeptides, and nucleic acid molecules of the invention may be used in the prevention and treatment of various thymus-related disorders. Examples of such disorders include tumors and cancers, hypoactivity, hyperactivity, atrophy, enlargement of the thymus, and the like. Other disorders include deregulation of T-lymphocyte selection or activity, and include but not be limited to disorders involving autoimmunity, arthritis, leukemias, lymphomas, immunosuppression, sepsis, wound healing, acute and chronic inflammation, cell mediated immunity, humor immunity, TH1/TH2 imbalance, and the like.

Other conditions that are treatable with a substance or compound identified in accordance with the methods described herein, antibodies, polypeptides, or nucleic acid molecules of the invention are proliferative disorders (e.g. microbial or parasitic infections), diabetes, disorders of the placenta, cardiomyopathy, liver disorders (e.g. chronic hepatitis, cancer of the liver, hepatic cirrhosis, cystic disease of the liver, Gilbert's Syndrome, Hepatitis A, B, or C, and toxic insults to the liver) and, kidney disorders (e.g. polycystic kidney disease, glomerulonephritis).

In addition, they may be used to modulate T-cell activation and immunodeficienty due to the Wiskott-Aldrich syndrome or AIDS, or to stimulate hematopoietic progenitor cell growth, and/or confer protection against chemotherapy and radiation therapy in a subject.

Accordingly, the substances, antibodies, and compounds may be formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regima may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions that may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances or compounds in association with one or more pharmaceutically acceptable vehicles or diluents, and contained in buffered solutions with a suitable pH and iso-osmotic with the physiological fluids.

After pharmaceutical compositions have been prepared, they can be placed in an appropriate container and labeled for treatment of an indicated condition. For administration of an inhibitor of a polypeptide of the invention, such labeling would include amount, frequency, and method of administration.

The compositions, substances, compounds, antibodies, etc. may be indicated as therapeutic agents either alone or in conjunction with other therapeutic agents (anti-proliferative agents, antimicrobial agents, immunostimulatory agents, or anti-inflammatories) or other forms of treatment (e.g. chemotherapy or radiotherapy). They can be administered concurrently, separately, or sequentially with other therapeutic agents or therapies.

The nucleic acid molecules encoding Core2c GlcNAc-T Polypeptides or any fragment thereof, or antisense sequences may be used for therapeutic purposes. Antisense to a nucleic acid molecule encoding a polypeptide of the invention may be used in situations to block the synthesis of the polypeptide. In particular, cells may be transformed with sequences complementary to nucleic acid molecules encoding Core 2c GlcNAc-T Polypeptide. Thus, antisense sequences may be used to modulate Core 2c GlcNAc-T activity or to achieve regulation of gene function. Sense or antisense oligomers or larger fragments, can be designed from various locations along the coding or regulatory regions of sequences encoding a polypeptide of the invention.

Expression vectors may be derived from retroviruses, adenoviruses, herpes or vaccinia viruses or from various bacterial plasmids for delivery of nucleic acid sequences to the target organ, tissue, or cells. Vectors that express antisense nucleic acid sequences of core 2c GlcNAc-T can be constructed using techniques well known to those skilled in the art (see for example, Sambrook et al. (supra)).

Genes encoding core2c GlcNAc-T can be turned off by transforming a cell or tissue with expression vectors that express high levels of a nucleic acid molecule or fragment thereof which encodes a polypeptide of the invention. Such constructs may be used to introduce untranslatable sense or antisense sequences into a cell. Even if they do not integrate into the DNA, the vectors may continue to transcribe RNA molecules until all copies are disabled by endogenous nucleases. Transient expression may last for extended periods of time (e.g a month or more) with a non-replicating vector or if appropriate replication elements are part of the vector system.

Modification of gene expression may be achieved by designing antisense molecules, DNA, RNA, or PNA, to the control regions of a core 2c GlcNAc-T gene i.e. the promoters, enhancers, and introns. Preferably the antisense molecules are oligonucleotides derived from the transcription initiation site (e.g. between positions −10 and +10 from the start site). Inhibition can also be achieved by using triple-helix base-pairing techniques. Triple helix pairing causes inhibition of the ability of the double helix to open sufficiently for the binding of polymerases, transcription factors, or regulatory molecules (see Gee J. E. et al (1994) In: Huber, B. E. and B. I. Carr, Molecular and Immunologic Approaches, Futura Publishing Co., Mt. Kisco, N.Y.). An antisense molecule may also be designed to block translation of mRNA by inhibiting binding of the transcript to the ribosomes.

Ribozymes, enzymatic RNA molecules, may be used to catalyze the specific cleavage of RNA. Ribozyme action involves sequence-specific hybridization of the ribozyme molecule to complementary target RNA, followed by endonucleolytic cleavage. For example, hammerhead motif ribozyme molecules may be engineered that can specifically and efficiently catalyze endonucleolytic cleavage of sequences encoding a polypeptide of the invention.

Specific ribosome cleavage sites within any RNA target may be initially identified by scanning the target molecule for ribozyme cleavage sites which include the following sequences: GUA, GUU, and GUC. Short RNA sequences of between 15 and 20 ribonucleotides corresponding to the region of the cleavage site of the target gene may be evaluated for secondary structural features which may render the oligonucleotide inoperable. The suitability of candidate targets may be evaluated by testing accessibility to hybridization with complementary oligonucleotides using ribonuclease protection assays.

Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The therapeutic index is the dose ratio of therapeutic to toxic effects and it can be expressed as the $ED_{50}/LD_{50}$ ratio. Pharmaceutical compositions which exhibit large therapeutic indices are preferred.

The invention also provides methods for studying the function of a Core2c GlcNAc-T polypeptide or a Core2c GlcNAc-T Related Polypeptide. Cells, tissues, and non-human animals lacking in core2c GlcNAc-T expression or partially lacking in core2c GlcNAc-T expression may be developed using recombinant expression vectors of the invention having specific deletion or insertion mutations in the core2c GlcNAc-T gene. A recombinant expression vector may be used to inactivate or alter the endogenous gene by homologous recombination, and thereby create a core2c GlcNAc-T deficient cell, tissue, or animal.

Null alleles may be generated in cells, such as embryonic stem cells by deletion mutation. A recombinant core2c GlcNAc-T gene may also be engineered to contain an insertion mutation which inactivates core2c GlcNAc-T Such a construct may then be introduced into a cell, such as an embryonic stem cell, by a technique such as transfection, electroporation, injection etc. Cells lacking an intact core2c GlcNAc-T gene may then be identified, for example by Southern blotting, Northern Blotting or by assaying for expression of a polypeptide of the invention using the methods described herein. Such cells may then be used to generate transgenic non-human animals deficient in core2c GlcNAc-T. Germline transmission of the mutation may be achieved, for example, by aggregating the embryonic stem cells with early stage embryos, such as 8 cell embryos, in vitro; transferring the resulting blastocysts into recipient females; and, generating germline transmission of the resulting aggregation chimeras. Such a mutant animal may be used to define specific cell populations, developmental patterns and in vivo processes, normally dependent on core2c GlcNAc-T expression.

The invention thus provides a transgenic non-human mammal all of whose germ cells and somatic cells contain a recombinant expression vector that inactivates or alters a gene encoding a Core2c GlcNAc-T polypeptide or a Core2c GlcNAc-T Related Polypeptide. Further the invention provides a transgenic non-human mammal which does not express or partially expresses a Core2c GlcNAc-T polypeptide or a Core2c GlcNAc-T Related Polypeptide of the invention.

A transgenic non-human animal includes but is not limited to mouse, rat, rabbit, guinea pig, micro-pig, pig, sheep, hamster, dog, cat, goat, and non-human primate, preferably mouse.

The invention also provides a transgenic non-human animal assay system which provides a model system for testing for an agent that reduces or inhibits a pathology associated with a Core2c GlcNAc-T polypeptide or a Core2c GlcNAc-T Related Polypeptide comprising:
  (a) administering the agent to a transgenic non-human animal of the invention; and
  (b) determining whether said agent reduces or inhibits the pathology in the transgenic non-human animal relative to a transgenic non-human animal of step (a) which has not been administered the agent.

The agent may be useful to treat the disorders and conditions discussed herein. The agents may also be incorporated in a pharmaceutical composition as described herein.

A polypeptide of the invention may be used to support the survival, growth, migration, and/or differentiation of cells expressing the polypeptide. Thus, a polypeptide of the invention may be used as a supplement to support, for example cells in culture.

Methods for Preparing Oligosaccharides

The invention relates to a method for preparing an oligosaccharide comprising contacting a reaction mixture comprising an activated GlcNAc and an acceptor in the presence of a polypeptide of the invention.

Examples of acceptors for use in the method for preparing an oligosaccharide are a saccharide, oligosaccharides, polysaccharides, glycopeptides, glycopolypeptides, or glycolipids which are either synthetic with linkers at the reducing end or naturally occurring structures, for example, asialo-agalacto-fetuin glycopeptide. The activated GlcNAc may be part of a nucleotide-sugar, a dolichol-phosphate-sugar, or dolichol-pyrophosphate-oligosaccharide.

In an embodiment of the invention, the oligosaccharides are prepared on a carrier that is non-toxic to a mammal, in particular a human such as a lipid isoprenoid or polyisoprenoid alcohol. An example of a suitable carrier is dolichol phosphate. The oligosaccharide may be attached to a carrier via a labile bond allowing for chemical removal of the oligosaccharide from the lipid carrier. In the alternative, the oligosaccharide transferase may be used to transfer the oligosaccharide form a lipid carrier to a polypeptide. The following non-limiting examples are illustrative of the present invention:

EXAMPLE 1

The cDNA sequence for human Core2 was used to search the GeneBank EST database whereby similarity matching displayed an EST cDNA clone of 47% identity/62% similarity (accession number AQ091453). This sequence was used as a template to generate primers for PCR isolation of this cDNA sequence from a genomic library. The primer sequences are as follows: 5'TTCAACAACTCCATCGT-TCAAGAC 3' (SEQ. ID. NO. 3) 5' TTCAACAACTC-CATCGTTCAAGAC 3' (SEQ. ID. NO. 4). A PCR reaction was performed using the following reagents: 5 µl of 10x PCR buffer (200 mM Tris-HCL (pH 84.), 500 mM KCl), 1.5 µl of 50 mM MgCl, 1 µl of 10 mM dNTP, 1 µl of each primer listed above (1 µg/µl), 1 µl of human genomic library DNA (Clontech #HL1067j) (diluted ¹/₂₀), 0.5 µl of Platinum Taq polymerase (5 U/µl-GIBCO-BRL) and $H_2O$ to a volume of 50 µl. The diluted genomic DNA library was boiled for 3 minutes prior to addition to the PCR reaction. The reaction conditions included 5 minutes of denaturation at 94° C. followed by 30 cycles of 94° C. for 1 minute, 60° C. for 1 minute and 72° C. for 1 minute with a final incubation at 72° C. for 10 minutes. A total of 20 tubes were assayed. The predicted size of this DNA is 222 base pairs which was isolated from the above PCR reaction and subcloned into the Bluescript vector using the T/A cloning method. This DNA fragment was sequence verified by the AGCT Corporation and named hcore2c. Two 3' end primers for hcore2c were generated [GTTGTACTGGATCTCACCTTCGA (SEQ. ID. NO. 5)/TCGAAGGTGAGATCCAGTACAAC (SEQ. ID. NO. 6)] and used with the SP6 and T7 primers for the amplification of the human genomic library which was cloned into the EMBL SP6/T7. The reaction conditions used were identical to that stated above with the following exceptions: 58° C. for 2 minutes, 72° C. for 3 minutes for 35 cycles. A 3' extension of hcore2c was isolated. Nucleotide sequences for human core 2c are shown in SEQ ID NO. 1 or 10 and amino acid sequences are shown in SEQ ID NO: 2 or 11. Mouse core 2c nucleotide and amino acid sequences are shown in SEQ ID NO: 7 and 8, respectively.

EXAMPLE 2

Expression of Core2c GlcNAc-T

Northern Blot Analysis of Human Tissues

Human multiple tissue cell line Northern blots were obtained from Clontech. All Northern blots contained 2 μg of mRNA/lane. These blots were hybridized with a PCR generated 316 bp fragment using the following primers: 5' primer TTCAACAACTCCATCGTTCAAGAC; 3' primer: TTCAACAACTCCATCGTTCAAGAC Amersham multiprime DNA labeling kit and [α-$^{32}$P]dCTP (3000 Ci/mol) were used for labeling. Northern blots were hybridized under stringent conditions following the recommended protocol (Clontech) and exposed to x-ray film or phosphoimager.

Results

Figure 2:
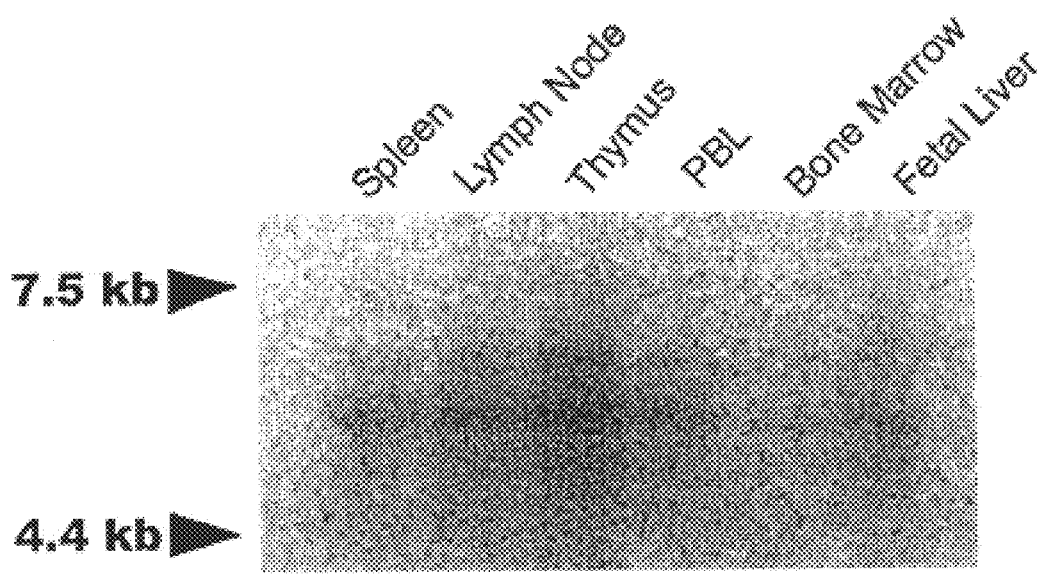
FIG. 2 is a blot showing expression of core 2c mRNA in the immune system.

The expression pattern of core2c GlcNAc-T was examined in different human tissues. Hybridization of Core2c GlcNAc-T cDNA probe to Northern blots under stringent conditions revealed the presence of core 2c GlcNAc-T mRNA in the placenta, liver (low expression), kidney, and thymus (FIG. 1). The core 2c GlcNAc-T mRNA was expressed in the thymus in the immune system (FIG. 2).

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

All publications, patents and patent applications referred to herein are incorporated by reference in their entirety to the same extent as if each individual publication, patent or patent application was specifically and individually indicated to be incorporated by reference in its entirety. All publications, patents and patent applications mentioned herein are incorporated herein by reference for the purpose of describing and disclosing the cell lines, vectors, methodologies etc. which are reported therein which might be used in connection with the invention. Nothing herein is to be construed as an admission that the invention is not entitled to antedate such disclosure by virtue of prior invention.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

We claim:

1. An isolated nucleic acid molecule which comprises:
   (i) a nucleic acid sequence of SEQ ID NO: 7,
   (ii) a nucleic acid sequence complementary to the full nucleic acid sequence of SEQ ID NO: 7, or
   (iii) a nucleic acid molecule which is a degenerate variant of SEQ ID NO: 7.

2. An isolated nucleic acid molecule which comprises:
   (i) a nucleic acid sequence of SEQ ID NO:9 or,
   (ii) a nucleic acid sequence complementary to the full nucleic acid sequence of SEQ ID NO:9.

3. The isolated nucleic acid molecule of claim 2 comprising or consisting essentially of the nucleic acid sequence of SEQ ID NO:9.

4. A vector comprising the nucleic acid molecule of claim 1.

5. A host cell comprising the nucleic acid molecule of claim 1.

6. An isolated nucleic acid molecule consisting of SEQ ID NO:7.

7. An isolated nucleic acid molecule consisting of SEQ ID NO:9.

8. A vector comprising the nucleic acid molecule of claim 6.

9. A vector comprising the nucleic acid molecule of claim 7.

10. A host cell comprising the nucleic acid molecule of claim 6.

11. A host cell comprising the nucleic acid molecule of claim 7.

12. An isolated nucleic acid molecule that is completely complementary to the nucleic acid molecule of claim 6.

13. An isolated nucleic acid molecule that is completely complementary to the nucleic acid molecule of claim 7.

14. A method for preparing the β-1,6,N-acetylglycosaminyltransferase of SEQ ID NO:8 comprising:
   (a) transfecting the vector of claim 8 into a host cell,
   (b) selecting transformed host cells from untransformed host cells,
   (c) culturing the selected transformed host cell under conditions which allow expression of the β-1,6,N-acetylglycosaminyltransferase, and
   (d) isolating the β-1,6,N-acetylglycosaminyltransferase.

* * * * *

SEQUENCE LISTING

```
<160> NUMBER OF SEQ ID NOS: 11

<210> SEQ ID NO 1
<211> LENGTH: 717
<212> TYPE: DNA
<213> ORGANISM: Unknown Sequence
<220> FEATURE:
<223> OTHER INFORMATION: Description of Unknown Sequence: DNA sequence
      of human or mouse core 2c
<221> NAME/KEY: modified_base
<222> LOCATION: (177)
<223> OTHER INFORMATION: a, t, c, g, other or unknown
<221> NAME/KEY: modified_base
<222> LOCATION: (675)
<223> OTHER INFORMATION: a, t, c, g, other or unknown

<400> SEQUENCE: 1
atatttgttg gcagtgctta ttttgttgta agtcaagcat ttgttaaata tattttcaac      60
aactccatcg ttcaagactt ttttgcctgg tctaaagaca catactctcc tgatgagcac    120
ttttgggcta ccttgattcg ggttccagga atacctgggg agatttccag atcagcncag    180
gatgtgtctg atctgcagag taagactcgc cttgtcaagt ggaattacta tgaaggcttt    240
ttctatccca gttgtactgg atctcacctt cgaagcgtgt gtatttatgg ggctggggac    300
ttgaattgga tgcttcagag ccatcacctg atggccaaca agtttgacgt aaacgtagat    360
gaaaatgctc ttcagtgctt agcagaatac ctacgttgga aggccatcta caggtgatgg    420
```

-continued

```
ctgctattgg cgaagtggcg gggcagaatc ctcctgcatc tcaccttgct cctgccgaga    480
aagtaaccat catggctgat gcaatgcggc ggctgcatac gcttgatccg gctacctgcc    540
cattcgacca ccaagcgaaa catcgcatcg agcgagcacg tactcggatg gaagccggtc    600
ttgtcgatca ggatgatctg gacgaagagc atcagggctc gcgccagccg aactgttcgc    660
caggctcaag gcgcncatgc ccgacggcga ggatctcgtc gtgacccatg gcgatgc       717
```

<210> SEQ ID NO 2
<211> LENGTH: 237
<212> TYPE: PRT
<213> ORGANISM: Unknown Sequence
<220> FEATURE:
<223> OTHER INFORMATION: Description of Unknown Sequence: amino acid
  sequence of human or mouse core 2c

<400> SEQUENCE: 2

```
Ile Phe Val Gly Ser Ala Tyr Phe Val Val Ser Gln Ala Phe Val Lys
  1               5                   10                  15

Tyr Ile Phe Asn Asn Ser Ile Val Gln Asp Phe Phe Ala Trp Ser Lys
                 20                  25                  30

Asp Thr Tyr Ser Pro Asp Glu His Phe Trp Ala Thr Leu Ile Arg Val
             35                  40                  45

Pro Gly Ile Pro Gly Glu Ile Ser Arg Ser Ala Gln Asp Val Ser Asp
         50                  55                  60

Leu Gln Ser Lys Thr Arg Leu Val Lys Trp Asn Tyr Tyr Glu Gly Phe
 65                  70                  75                  80

Phe Tyr Pro Ser Cys Thr Gly Ser His Leu Arg Ser Val Cys Ile Tyr
                 85                  90                  95

Gly Ala Gly Asp Leu Asn Trp Met Leu Gln Ser His His Leu Met Ala
            100                 105                 110

Asn Lys Phe Asp Val Asn Val Asp Glu Asn Ala Leu Gln Cys Leu Ala
        115                 120                 125

Glu Tyr Leu Arg Trp Lys Ala Ile Tyr Arg Trp Leu Leu Leu Ala Lys
    130                 135                 140

Trp Arg Gly Arg Ile Leu Leu His Leu Thr Leu Leu Leu Pro Arg Lys
145                 150                 155                 160

Pro Ser Trp Leu Met Gln Cys Gly Gly Cys Ile Arg Leu Ile Arg Leu
                165                 170                 175

Pro Ala His Ser Thr Thr Lys Arg Asn Ile Ala Ser Ser Glu His Val
            180                 185                 190

Leu Gly Trp Lys Pro Val Leu Ser Ile Arg Met Ile Trp Thr Lys Ser
        195                 200                 205

Ile Arg Ala Arg Ala Ser Arg Thr Val Arg Gln Ala Gln Gly Ala His
    210                 215                 220

Ala Arg Arg Arg Gly Ser Arg Arg Asp Pro Trp Arg Cys
225                 230                 235
```

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 3

```
ttcaacaact ccatcgttca agac                                            24
```

```
<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 4
acgcttcgaa ggtgagatcc agtac                                       25

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 5
gttgtactgg atctcacctt cga                                         23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 6
tcgaaggtga gatccagtac aac                                         23

<210> SEQ ID NO 7
<211> LENGTH: 1368
<212> TYPE: DNA
<213> ORGANISM: Mus sp.

<400> SEQUENCE: 7
atgaagatat tcagatgttg ctttaaatac actctccagc agaaactctt catcctcctc    60
ttaaccctgt ggctgttctc cttgttgaag ctcctaaatg tgggcaggct cctcttccct   120
caaagagaca tttacttagt tgaatactcc ctaagtacat caccatttgt gaggaacagg   180
ttccccgagt ctggggatgc agccaggac aacgttaact gctcgggggt ctacgagcac   240
gagcctttgg aaatcggcaa gagtctagaa atcagaagac ggagcatcat cgacttggag   300
gacggtgatg tcgtggcgat gacaagtgac tgtgacgttt atcagaccct aaggcagtac   360
catgaaaagc tggtttcaag ggaggaagag gacttcccca tagcctattc gctggtcgtc   420
cacaaagatg ccattatggt tgagcggttg atccgagcta tttacaacca gcacaacctt   480
tactgcatcc attatgacct gaagtcaccg gacacgttca agctgccat gaacaaccta   540 gctaagtgct tccccaatat cttcatcgct tccaaattag agactgtgga gtatgctcac   600
atatccaggc tccaggccga ttggaactgc ttatcagacc cctcaagtc ttccgttcag   660 tggaagtacg tcatcaacct ctgtgggcaa gactttcccc taaagtcaaa ttttgaatta   720
gtgacagagc tgaaaagtct ccaaggaagg aatatgttag agacggtgag acccccagt   780 gctaagacgg agaggttcac ctaccatcat gagctcagac aggtgcctta tgattatatg   840
aagctaccag taaagacgaa cgtctccaag ggggcacccc ctcataacat tcaggtattt   900
gtgggcagtg cctattttgt tttaagtcga gcatttgtta aatatatttt caacagctcc   960
ctcgttgaag acttttttgc ctggtctaaa gatacatatt ctcctgacga gcacttttgg  1020
gccaccttaa tccggatacc aggaataccc ggggaattt ccagttcatc tcaggacgtg  1080
```

-continued

```
tctgacctgc agagtaagac ccgcctggtc aaatggtttt actacgaagg ctttctctac    1140
cccaattgca ctggctctca ccttcgaagt gtgtgtattt acggagctgc agaactacgg    1200
tggctcttaa acgaagggca ttggtttgct aataagtttg attctaaagt tgaccccatc    1260
ttgatgaaat gtctggcaga aaaacttgaa gagcaacaga gaaagttgat tgctttgtct    1320
tcagagaagt tcatgacaga gggaacccgc caaagccaca cattataa                 1368
```

<210> SEQ ID NO 8
<211> LENGTH: 455
<212> TYPE: PRT
<213> ORGANISM: Mus sp.

<400> SEQUENCE: 8

```
Met Lys Ile Phe Arg Cys Cys Phe Lys Tyr Thr Leu Gln Gln Lys Leu
  1               5                  10                  15

Phe Ile Leu Leu Leu Thr Leu Trp Leu Phe Ser Leu Leu Lys Leu Leu
                 20                  25                  30

Asn Val Gly Arg Leu Leu Phe Pro Gln Arg Asp Ile Tyr Leu Val Glu
             35                  40                  45

Tyr Ser Leu Ser Thr Ser Pro Phe Val Arg Asn Arg Phe Pro Glu Ser
         50                  55                  60

Gly Asp Ala Ala Arg Asp Asn Val Asn Cys Ser Gly Val Tyr Glu His
 65                  70                  75                  80

Glu Pro Leu Glu Ile Gly Lys Ser Leu Glu Ile Arg Arg Arg Ser Ile
                 85                  90                  95

Ile Asp Leu Glu Asp Gly Asp Val Val Ala Met Thr Ser Asp Cys Asp
            100                 105                 110

Val Tyr Gln Thr Leu Arg Gln Tyr His Glu Lys Leu Val Ser Arg Glu
        115                 120                 125

Glu Glu Asp Phe Pro Ile Ala Tyr Ser Leu Val Val His Lys Asp Ala
    130                 135                 140

Ile Met Val Glu Arg Leu Ile Arg Ala Ile Tyr Asn Gln His Asn Leu
145                 150                 155                 160

Tyr Cys Ile His Tyr Asp Leu Lys Ser Pro Asp Thr Phe Lys Ala Ala
                165                 170                 175

Met Asn Asn Leu Ala Lys Cys Phe Pro Asn Ile Phe Ile Ala Ser Lys
            180                 185                 190

Leu Glu Thr Val Glu Tyr Ala His Ile Ser Arg Leu Gln Ala Asp Trp
        195                 200                 205

Asn Cys Leu Ser Asp Leu Leu Ser Ser Val Gln Trp Lys Tyr Val
    210                 215                 220

Ile Asn Leu Cys Gly Gln Asp Phe Pro Leu Lys Ser Asn Phe Glu Leu
225                 230                 235                 240

Val Thr Glu Leu Lys Ser Leu Gln Gly Arg Asn Met Leu Glu Thr Val
                245                 250                 255

Arg Pro Pro Ser Ala Lys Thr Glu Arg Phe Thr Tyr His His Glu Leu
            260                 265                 270

Arg Gln Val Pro Tyr Asp Tyr Met Lys Leu Pro Val Lys Thr Asn Val
        275                 280                 285

Ser Lys Gly Ala Pro Pro His Asn Ile Gln Val Phe Val Gly Ser Ala
    290                 295                 300

Tyr Phe Val Leu Ser Arg Ala Phe Val Lys Tyr Ile Phe Asn Ser Ser
305                 310                 315                 320
```

```
Leu Val Glu Asp Phe Phe Ala Trp Ser Lys Asp Thr Tyr Ser Pro Asp
                325                 330                 335

Glu His Phe Trp Ala Thr Leu Ile Arg Ile Pro Gly Ile Pro Gly Gly
            340                 345                 350

Ile Ser Ser Ser Ser Gln Asp Val Ser Asp Leu Gln Ser Lys Thr Arg
        355                 360                 365

Leu Val Lys Trp Phe Tyr Tyr Glu Gly Phe Leu Tyr Pro Asn Cys Thr
    370                 375                 380

Gly Ser His Leu Arg Ser Val Cys Ile Tyr Gly Ala Ala Glu Leu Arg
385                 390                 395                 400

Trp Leu Leu Asn Glu Gly His Trp Phe Ala Asn Lys Phe Asp Ser Lys
                405                 410                 415

Val Asp Pro Ile Leu Met Lys Cys Leu Ala Glu Lys Leu Glu Glu Gln
            420                 425                 430

Gln Arg Lys Leu Ile Ala Leu Ser Ser Glu Lys Phe Met Thr Glu Gly
        435                 440                 445

Thr Arg Gln Ser His Thr Leu
    450                 455

<210> SEQ ID NO 9
<211> LENGTH: 2060
<212> TYPE: DNA
<213> ORGANISM: Mus sp.

<400> SEQUENCE: 9
cgtcgacagg gagggcgttc tgtgttgatc cgcacccgtc tttcctaacg attcactaaa      60
caggtttcag ggcctctccc gccactgttt cgttgagtgc agacgataag gtgagacccg     120
aggccccgcc gtcctgagcg ggaaccagcc tacgtcgccc gagaggtccc gctccggtcg     180
tagccggtcg cgacggatcg gtccgcaata gtcgcctcac ccttccacct cacaacgtct     240
gattaatccc atgtttcaac acaaaattag tcacggatgt acgccttatg cgaaggagaa     300 agggaggcc gccccccact ctttctccca ctacgacgta ggccggccca acctcaagag     360
tctttctgac gacctttttt ccatgtgcgg gtaatttggt tgacccgtcg tactgagggt     420
cccaggaaca attccccgga acacacaaac gaatgtaaca tttcgtccgt gacatccaca     480
cattcactaa gtgggggtttc ccggaaggat caccccacag tctccctctg aaggacctta     540
gacgggcgtc ttgttctcat cgtgattcgt tctgtcagcg ttaaccgaac aagaaatgac     600
aaggtagaaa ttttacctga ctccgacgcc gtacgaaccg cccgaccact cttcgaccca     660
tcctgagtct taggtctaag tcagttaagg cttcacagcc tgatagagtc ggctctcgag     720
gtcaaaggga tgtaaccgaa attttttcaca cgttcagggt cctagtctcc tagtctccat     780
ccgcctagtc tccactcctg tgttgtagac aggggttgtg ggcctcattg actctggtcg     840
ccctgggtcc gtgggtcctt gaggcggtct ggtcaccgta cccaaggaag accagacaga     900
cccaaccgca ggaacccgag tttgagacgt cggtcggggt gtcgtcggtc accgtcgagg     960
tgagaatccg tgagattgag tgggtcctag tctcctaggg tcctagggtc ctcaaaccag    1020
tgtgatccta gagttccagg gtttccgtcg aactgatggt ctcgagcctg tgtgggtcct    1080
agagcctgtg tgggtcctag agtcctagcg ttctagggtc ttagtgttct agggtctctg    1140
tcgaactgaa cctccttaag actgtgttgg tcctagtgtc cttcctgtcc gaggtcagtc    1200
agtcccgtcc atcgtgatct ttattggtct atcaccctcc gttcacattc ttgtcgttgt    1260
ctttggttcc aatgaactgt agtagtcttg ggttaagagg gtggtatcgt tcaggaccta    1320
```

-continued

```
tgggggttgtg tagcccttc gttctaagtc tagattttag tgaagagtac tactatctcc    1380
tgtaattctt cctgtatttta ttgagggaat ttctttatgt cctcttgtgt ccatttgtcg    1440
atctcgggga tttctccttt gtgttttttag ggaatttctc aatgtccttt tgtgttagtt    1500
tgtccacttc ctttccttgt tttggtaggc cttagatttt tacctttatc tttgttattt    1560
ctttagtgtt tccctctgtt ggaacctcaa ttttttggat cctttctgta gtcctcagta    1620
tctacgttcg tagtggttgt cttatgttct ctatcttcac tcttagagtc cccgtcttct    1680
atggtatctt ttgtaactgt gtagtttctt ttacgttttt cgttttccga ggattgggtt    1740
ttgtaggtcc tttaggtcct gtgttactct tctcgtttgg attcctatta tctacatctt    1800
ctctcacttc taagggttga atttcccggt catttataga agttgtttta atatcttctt    1860
ttgaagggat tggatttctt tctccacggg tgcttgtatg ttcttcggat gtcttgaggt    1920
ttatctgaac tggtcttttc tttaaggagg acagtgtatt attagttttg tggtttacat    1980
gatttgtttc ttaaaattt cgtcattccc ttttttccagt tcattgtata tttccgtctg    2040
gatagtcttt atatggtctg                                                 2060
```

<210> SEQ ID NO 10
<211> LENGTH: 3435
<212> TYPE: DNA
<213> ORGANISM: Homo sapiens

<400> SEQUENCE: 10

```
tcaatgcact gttcaaggat gtttgagaga ttttctgtct tgcctgaata caaaacactg      60
tagggaacct cttgtgcttg actttgcaca cacgggat cttcagggtg ggtacattta       120
aaactgacaa gtattgccaa attgccccc aacgtagttt tacaccccca cctactactc      180
tcagtgaaaa atcaggccct ttttatttta agggctaaat tgctaatccc tgtgtgaaaa     240
tgggtgttaa caaaataaaa aataaggaaa atatgcaggc ttacccaatt ttgttatcta     300
tacatttac agtctctaat acttagcata gctcctttgg gtgtctgccc accacccttc     360
tttctgaacg tgggggttccc tgggctttcc ttgtttgact tcagacctgg atctaatagg    420
gatctggagg tagaatcaag acgaatgttc cctttggcct taggtgagtc ctttgcatct     480
ctgaggcct gttgatgaca tccagttctc tagacctctg cccaaaccag agcaatccct      540
cctcaaatat gctaagcaga atgcagaca atataagaca cactatattt atatttaggg     600
agtttacatt accttccctt ctgtttggaa accaacatct ctcaaaatta ggtatagtta     660
acacagaata ccccaaaata ccaccattct tcataattcc atttccttat ttctggattc     720
tttcaagggt aaaaaccttg tttcattcat ctttggggca gcatttgcct agtatgtggt     780
aggcgcccag tagattttgg ataaactgac ctgattttct gttaatattc caactggatt    840
attctttct cctcttacag aatgaagata ttcaaatgtt attttaaaca taccctacag      900
cagaaagttt tcatcctgtt tttaacccta tggctgctct ctttgttaaa gcttctaaat    960
gtgagacgac tctttccgca aaaagacatt tacttggttg agtactccct aagtacctcg    1020
ccttttgtaa gaaacagata cactcatgtt aaggatgaag tcaggtatga agttaactgt    1080
tcgggtatct atgaacagga gcctttggaa attggaaaga gtctggaaat aagaagaagg    1140
gacatcattg acttggagga tgatgatgtt gtggcaatga ccagtgattg tgacatttat    1200
cagactctaa gaggttatgc tcaaaagctt gtctcaaagg aggagaaaag cttcccaata    1260
gcctattctt tggttgtcca caaagatgca attatgggtt aaaggcttat ccatgctata    1320
tacaaccagc acaatattta ctgcatccat tatgatcgta aggcacctga taccttcaaa    1380
```

-continued

| | |
|---|---|
| gttgccatga acaatttagc taagtgcttc tccatatttt tcattgcttc caaattagag | 1440 |
| gctgtggaat atgcccacat ttccagactc caggctgatt taaattgctt gtcggacctt | 1500 |
| ctgaagtctt caatccagtg gaaatatgtt atcaacttgt gtgggcaaga ttttcccctg | 1560 |
| aagtcaaatt ttgaattggt gtcagagttg aaaaaactca atggagcaaa tatgttggag | 1620 |
| acggtgaaac ccccaaacag taaattggaa agattcactt accatcatga acttagacgg | 1680 |
| gtgccttatg aatatgtgaa gctaccaata aggacaaaca tctccaagga agcaccccccc | 1740 |
| cataacattc agatatttgt tggcagtgct tattttgttt taagtcaagc atttgttaaa | 1800 |
| tatattttca acaactccat cgttcaagac tttttgcct ggtctaaaga cacatactct | 1860 |
| cctgatgagc acttttgggc taccttgatt cgggttccag gaatacctgg ggagatttcc | 1920 |
| agatcagccc aggatgtgtc tgatctgcag agtaagactc gccttgtcaa gtggaattac | 1980 |
| tatgaaggct ttttctatcc cagttgtact ggatctcacc ttcgaagcgt gtgtatttat | 2040 |
| ggagctgcag aattaaggtg gcttatcaaa gatggacatt ggtttgctaa taaatttgat | 2100 |
| tctaaggtgg accctatctt gattaaatgc ttggcagaaa agcttgaaga acagcagaga | 2160 |
| gactggatca ctttgccctc agaaaagtta tttatggata gaaatctcac taccacatca | 2220 |
| tgatagtaaa atcaggatgg aaataagagg gtgcctgata aatggagtca gtgtggaatt | 2280 |
| gaataccata ctatgcccaa tactgtttaa actcagtcct cccatatttt aaaaggtgtc | 2340 |
| caaaattcca tacacaaggg aaagtgatct agcctttgat gttattagcc tgcagttggc | 2400 |
| taggtttttt taatatttgt ttttgcttgt aatctcactg agccaaatca gagatcttaa | 2460 |
| acattcagtc agtcatcaaa cattattgag cacctaacta tatgacaggc actttttag | 2520 |
| agactgcggc ttatcctcat catagcaacc tcggtatctt taagttctcc acataacagt | 2580 |
| caggattcta ctgaagaagc ttttgaagtt tgtggtaatc gtctgatcat ataaaccacc | 2640 |
| catttcagag tagtgtttaa gtactgtgac caacactcca cttgtctctt aactcagctt | 2700 |
| tcaagacatt ccttaaccat cagagcagag gaggaaagac tcactacctc agaaaaatct | 2760 |
| caaagaatag tccaatttcc tgcttgccaa agcataatct gcctttggt gcattacttg | 2820 |
| gtcaattcag ggttgaggag actgttgggg ggcatttata atgtatgaaa gttaaggaag | 2880 |
| ggggtgagga tgtgggttgg acaggtagt acctaaagag gagcgaaggg atttatacaa | 2940 |
| catttttatc atgttacaaa acagtatcat gaatggcctc cttttagtt caactgtttc | 3000 |
| tttaaaatgc atttactgat taaaaataag aactgaccaa tagctccaag tgtcacacac | 3060 |
| cagaacatta agcctaagtc ctcaattcat aagttatcat tctagacaag tttctttaca | 3120 |
| atgaatact ttctatggaa tcattataat tctgttgtgt ggaactatca agctaagagt | 3180 |
| cactaaactt tcttgaaaag gttgtgtgaa atatgacagc tttctaaatt aatttgtata | 3240 |
| gtcatttaaa atttttcctt ctctggcaac tgtccaactg gaatccagat ttaaggtgat | 3300 |
| aaaagctcta agtttcttgc agtctttttc tcagcttagt tccagagaga aaaagctaa | 3360 |
| ttttcctaag gacacagcaa gaatattcat taaggatatt ttctaaaacc cacacttgag | 3420 |
| aaaaccaccc aatga | 3435 |

<210> SEQ ID NO 11
<211> LENGTH: 1104
<212> TYPE: PRT
<213> ORGANISM: Homo sapiens

```
<400> SEQUENCE: 11

Ser Met His Cys Ser Arg Met Phe Glu Arg Phe Ser Val Leu Pro Glu
  1               5                  10                  15

Tyr Lys Thr Leu Gly Thr Ser Cys Ala Leu Cys Thr His Thr Gly Ser
             20                  25                  30

Ser Gly Trp Val His Leu Lys Leu Thr Ser Ile Ala Lys Leu Pro Pro
             35                  40                  45

Asn Val Val Phe Thr Pro His Leu Leu Leu Ser Val Lys Asn Gln Ala
         50                  55                  60

Leu Phe Ile Leu Arg Ala Lys Leu Leu Ile Pro Val Lys Trp Val Leu
 65                  70                  75                  80

Thr Lys Lys Ile Arg Lys Ile Cys Arg Leu Thr Gln Phe Cys Tyr Leu
                 85                  90                  95

Tyr Ile Leu Gln Ser Leu Ile Leu Ser Ile Ala Pro Leu Gly Val Cys
                100                 105                 110

Pro Pro Pro Phe Phe Leu Asn Val Gly Phe Pro Gly Leu Ser Leu Phe
            115                 120                 125

Asp Phe Arg Pro Gly Ser Asn Arg Asp Leu Glu Val Glu Ser Arg Arg
            130                 135                 140

Met Phe Pro Leu Ala Leu Gly Glu Ser Phe Ala Ser Leu Arg Pro Cys
145                 150                 155                 160

His Pro Val Leu Thr Ser Ala Gln Thr Arg Ala Ile Pro Pro Gln Ile
                165                 170                 175

Cys Ala Glu Met Gln Thr Ile Asp Thr Leu Tyr Leu Tyr Phe Arg Ser
                180                 185                 190

Leu His Tyr Leu Pro Phe Cys Leu Glu Thr Asn Ile Ser Gln Asn Val
            195                 200                 205

Leu Thr Gln Asn Thr Pro Lys Tyr His His Ser Ser Phe His Phe Leu
210                 215                 220

Ile Ser Gly Phe Phe Gln Gly Lys Pro Cys Phe Ile His Leu Trp Gly
225                 230                 235                 240

Ser Ile Cys Leu Val Cys Gly Arg Arg Pro Val Asp Phe Gly Thr Asp
                245                 250                 255

Leu Ile Phe Cys Tyr Ser Asn Trp Ile Ile Ser Phe Ser Ser Tyr Arg
                260                 265                 270

Met Lys Ile Phe Lys Cys Tyr Phe Lys His Thr Leu Gln Gln Lys Val
                275                 280                 285

Phe Ile Leu Phe Leu Thr Leu Trp Leu Leu Ser Leu Leu Lys Leu Leu
290                 295                 300

Asn Val Arg Arg Leu Phe Pro Gln Lys Asp Ile Tyr Leu Val Glu Tyr
305                 310                 315                 320

Ser Leu Ser Thr Ser Pro Phe Val Arg Asn Arg Tyr Thr His Val Lys
                325                 330                 335

Asp Glu Val Arg Tyr Glu Val Asn Cys Ser Gly Ile Tyr Glu Gln Glu
                340                 345                 350

Pro Leu Glu Ile Gly Lys Ser Leu Glu Ile Arg Arg Asp Ile Ile
            355                 360                 365

Asp Leu Glu Asp Asp Val Val Ala Met Thr Ser Asp Cys Asp Ile
370                 375                 380

Tyr Gln Thr Leu Arg Gly Tyr Ala Gln Lys Leu Val Ser Lys Glu Glu
385                 390                 395                 400

Lys Ser Phe Pro Ile Ala Tyr Ser Leu Val Val His Lys Asp Ala Ile
            405                 410                 415
```

-continued

```
Met Val Glu Arg Leu Ile His Ala Ile Tyr Asn Gln His Asn Ile Tyr
            420                 425                 430

Cys Ile His Tyr Asp Arg Lys Ala Pro Asp Thr Phe Lys Val Ala Met
        435                 440                 445

Asn Asn Leu Ala Lys Cys Phe Ser Asn Ile Phe Ile Ala Ser Lys Leu
450                 455                 460

Glu Ala Val Glu Tyr Ala His Ile Ser Arg Leu Gln Ala Asp Leu Asn
465                 470                 475                 480

Cys Leu Ser Asp Leu Leu Lys Ser Ser Ile Gln Trp Lys Tyr Val Ile
                485                 490                 495

Asn Leu Cys Gly Gln Asp Phe Pro Leu Lys Ser Asn Phe Glu Leu Val
                500                 505                 510

Ser Glu Leu Lys Lys Leu Asn Gly Ala Asn Met Leu Glu Thr Val Lys
            515                 520                 525

Pro Pro Asn Ser Lys Leu Glu Arg Phe Thr Tyr His His Glu Leu Arg
        530                 535                 540

Arg Val Pro Tyr Glu Tyr Val Lys Leu Pro Ile Arg Thr Asn Ile Ser
545                 550                 555                 560

Lys Glu Ala Pro Pro His Asn Ile Gln Ile Phe Val Gly Ser Ala Tyr
                565                 570                 575

Phe Val Leu Ser Gln Ala Phe Val Lys Tyr Ile Phe Asn Asn Ser Ile
                580                 585                 590

Val Gln Asp Phe Phe Ala Trp Ser Lys Asp Thr Tyr Ser Pro Asp Glu
        595                 600                 605

His Phe Trp Ala Thr Leu Ile Arg Val Pro Gly Ile Pro Gly Glu Ile
        610                 615                 620

Ser Arg Ser Ala Gln Asp Val Ser Asp Leu Gln Ser Lys Thr Arg Leu
625                 630                 635                 640

Val Lys Trp Asn Tyr Tyr Glu Gly Phe Phe Tyr Pro Ser Cys Thr Gly
                645                 650                 655

Ser His Leu Arg Ser Val Cys Ile Tyr Gly Ala Ala Glu Leu Arg Trp
            660                 665                 670

Leu Ile Lys Asp Gly His Trp Phe Ala Asn Lys Phe Asp Ser Lys Val
            675                 680                 685

Asp Pro Ile Leu Ile Lys Cys Leu Ala Glu Lys Leu Glu Glu Gln Gln
690                 695                 700

Arg Asp Trp Ile Thr Leu Pro Ser Glu Lys Leu Phe Met Asp Arg Asn
705                 710                 715                 720

Leu Thr Thr Thr Ser Asn Gln Asp Gly Asn Lys Arg Val Pro Asp Lys
                725                 730                 735

Trp Ser Gln Cys Gly Ile Glu Tyr His Thr Met Pro Asn Thr Val Thr
            740                 745                 750

Gln Ser Ser His Ile Leu Lys Gly Val Gln Asn Ser Ile His Lys Gly
        755                 760                 765

Lys Ser Ser Leu Cys Tyr Pro Ala Val Gly Val Phe Leu Ile Phe Val
        770                 775                 780

Phe Ala Cys Asn Leu Thr Glu Pro Asn Gln Arg Ser Thr Phe Ser Gln
785                 790                 795                 800

Ser Ser Asn Ile Ile Glu His Leu Thr Ile Gln Ala Leu Phe Arg Leu
                805                 810                 815

Arg Leu Ile Leu Ile Ile Ala Thr Ser Val Ser Leu Ser Ser Pro His
            820                 825                 830
```

-continued

```
Asn Ser Gln Asp Ser Thr Glu Glu Ala Phe Glu Val Cys Gly Asn Arg
        835                 840                 845

Leu Ile Ile Thr Thr His Phe Arg Val Val Phe Lys Tyr Cys Asp Gln
    850                 855                 860

His Ser Thr Cys Leu Leu Thr Gln Leu Ser Arg His Ser Leu Thr Ile
865                 870                 875                 880

Arg Ala Glu Glu Glu Arg Leu Thr Thr Ser Glu Lys Ser Gln Arg Ile
                885                 890                 895

Val Gln Phe Pro Ala Cys Gln Ser Ile Ile Cys Leu Leu Val His Tyr
                900                 905                 910

Leu Val Asn Ser Gly Leu Arg Arg Leu Leu Gly Gly Ile Tyr Asn Val
        915                 920                 925

Lys Leu Arg Lys Gly Val Arg Met Trp Val Gly Thr Gly Ser Thr Arg
    930                 935                 940

Gly Ala Lys Gly Phe Ile Gln His Phe Tyr His Val Thr Lys Gln Tyr
945                 950                 955                 960

His Glu Trp Pro Pro Phe Phe Asn Cys Phe Phe Lys Met His Leu Leu
                965                 970                 975

Ile Lys Asn Lys Asn Pro Ile Ala Pro Ser Val Thr His Gln Asn Ile
            980                 985                 990

Lys Pro Lys Ser Ser Ile His Lys Leu Ser Phe Thr Ser Phe Phe Thr
        995                 1000                1005

Met Glu Tyr Phe Leu Trp Asn His Tyr Asn Ser Val Val Trp Asn Tyr
    1010                1015                1020

Gln Ala Lys Ser His Thr Phe Leu Lys Arg Leu Cys Glu Ile Gln Leu
1025                1030                1035                1040

Ser Lys Leu Ile Cys Ile Val Ile Asn Phe Phe Ser Gly Asn Cys
                1045                1050                1055

Pro Thr Gly Ile Gln Ile Gly Asp Lys Ser Ser Lys Phe Leu Ala Val
            1060                1065                1070

Phe Phe Ser Ala Phe Gln Arg Glu Lys Ser Phe Ser Gly His Ser Lys
        1075                1080                1085

Asn Ile His Gly Tyr Phe Leu Lys Pro Thr Leu Glu Lys Thr Thr Gln
    1090                1095                1100
```